(12) United States Patent
Saunier et al.

(10) Patent No.: US 7,648,536 B2
(45) Date of Patent: *Jan. 19, 2010

(54) METHOD OF COLORING KERATINOUS FIBERS COMPRISING APPLICATION OF AT LEAST ONE AMINOPYRAZOLOPYRIDINE OXIDATION BASE IN THE ABSENCE OF CHEMICAL OXIDIZING AGENTS

(75) Inventors: Jean-Baptiste Saunier, Paris (FR); Aziz Fadli, Chelles (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/149,871

(22) Filed: May 9, 2008

(65) Prior Publication Data

US 2008/0289121 A1 Nov. 27, 2008

Related U.S. Application Data

(60) Provisional application No. 60/924,851, filed on Jun. 1, 2007.

(30) Foreign Application Priority Data

May 9, 2007 (FR) .................................. 07 54948

(51) Int. Cl.
 *A61Q 5/10* (2006.01)
(52) U.S. Cl. ................... 8/405; 8/406; 8/409; 8/411; 8/435; 8/568; 8/570; 8/571; 8/670; 132/202; 132/208
(58) Field of Classification Search .............. 8/405, 8/406, 409, 411, 435, 568, 570, 571, 670; 132/202, 208
See application file for complete search history.

(56) References Cited

U.S. PATENT DOCUMENTS

| | | | |
|---|---|---|---|
| 2,841,584 A | 7/1958 | Hunter et al. | |
| 4,003,699 A | 1/1977 | Rose et al. | |
| 4,128,425 A | 12/1978 | Greenwald | |
| RE30,199 E | 1/1980 | Rose et al. | |
| 4,823,985 A | 4/1989 | Grollier et al. | |
| 5,061,289 A | 10/1991 | Clausen et al. | |
| 5,234,818 A | 8/1993 | Zimmermann et al. | |
| 5,380,340 A | 1/1995 | Neunhoeffer et al. | |
| 5,457,200 A | 10/1995 | Zimmermann et al. | |
| 5,534,267 A | 7/1996 | Neunhoeffer et al. | |
| 5,663,366 A | 9/1997 | Neunhoeffer et al. | |
| 5,766,576 A | 6/1998 | Löwe et al. | |
| 6,027,538 A | 2/2000 | Vandenbossche et al. | |
| 6,099,592 A | 8/2000 | Vidal et al. | |
| 6,099,593 A | 8/2000 | Terranova et al. | |
| 6,284,003 B1 | 9/2001 | Rose et al. | |
| 6,338,741 B1 | 1/2002 | Vidal et al. | |
| 6,645,258 B2 | 11/2003 | Vidal et al. | |
| 6,730,789 B1 * | 5/2004 | Birault et al. | ............... 546/121 |
| 7,091,215 B2 | 8/2006 | Hibi et al. | |
| 7,285,666 B2 | 10/2007 | Hibi et al. | |
| 2002/0032934 A1 | 3/2002 | Kravtchenko et al. | |
| 2006/0277691 A1 | 12/2006 | Saunier | |
| 2006/0277693 A1 | 12/2006 | Saunier | |
| 2007/0136959 A1 | 6/2007 | Fadli | |
| 2007/0143935 A1 | 6/2007 | Fadli et al. | |

FOREIGN PATENT DOCUMENTS

| | | |
|---|---|---|
| DE | 23 59 399 A1 | 6/1975 |
| DE | 38 43 892 A1 | 6/1990 |
| DE | 41 33 957 A1 | 4/1993 |
| DE | 195 43 988 A1 | 5/1997 |
| EP | 0 433 854 | 6/1991 |
| EP | 0 770 375 | 5/1997 |
| EP | 1 155 680 | 11/2001 |
| EP | 1 233 743 | 8/2002 |
| EP | 1 389 618 | 2/2004 |
| EP | 1 586 302 | 10/2005 |
| EP | 1 733 714 | 12/2006 |
| EP | 1 792 606 | 6/2007 |
| EP | 1 792 903 | 6/2007 |
| FR | 2 586 913 | 3/1987 |
| FR | 2 733 749 | 11/1996 |
| FR | 2 750 048 | 12/1997 |
| FR | 2 767 475 | 2/1999 |
| FR | 2 801 308 | 5/2001 |
| FR | 2 822 689 | 10/2002 |
| FR | 2 822 690 | 10/2002 |
| FR | 2 822 691 | 10/2002 |
| FR | 2 822 692 | 10/2002 |
| FR | 2 886 137 | 12/2006 |
| FR | 2 886 139 | 12/2006 |
| GB | 1 026 978 | 4/1966 |
| GB | 1 153 196 | 5/1969 |
| JP | 2-019576 | 1/1990 |

(Continued)

OTHER PUBLICATIONS

Boros, E. et al., "A Convenient Synthesis of Pyrazolidine and 3-Amino-6, 7-dihydro-1H, 5H-pyrazolo[1,2-a]pyrazol-1-one". J. Heterocyclic Chem, 38, 2001, pp. 613-616.

Cohen, S. et al., "Bicyclic, Cyclic, and Acyclic Azo Compounds, 2,3-Diazabicyclo[2,2,2]-2-octene, 3,6-Dimethyl-delta-tetrahydropyridazine and Aziosopropane". J. Am. Chem. Soc., 84, 1962, pp. 586-591.

Co-pending U.S. Appl. No. 11/594,957, filed Nov. 9, 2006.
Co-pending U.S. Appl. No. 11/594,967, filed Nov. 9, 2006.

(Continued)

*Primary Examiner*—Eisa B Elhilo
(74) *Attorney, Agent, or Firm*—Finnegan, Henderson, Farabow, Garrett & Dunner LLP

(57) ABSTRACT

Disclosed herein are methods for coloring keratinous fibers comprising applying to the fibers a dyeing composition comprising at least one aminopyrazolopyridine base, said coloring method being performed without the addition of chemical oxidizing agents.

11 Claims, No Drawings

FOREIGN PATENT DOCUMENTS

| | | |
|---|---|---|
| JP | 5-163124 | 6/1993 |
| JP | 2526099 | 8/1996 |
| WO | WO 94/08969 | 4/1994 |
| WO | WO 94/08970 | 4/1994 |
| WO | WO 96/15765 | 5/1996 |
| WO | WO 01/35917 | 5/2001 |
| WO | WO 02/076416 | 10/2002 |
| WO | WO 02/076417 | 10/2002 |
| WO | WO 02/076418 | 10/2002 |

OTHER PUBLICATIONS

Co-pending U.S. Appl. No. 12/149,872, filed May 9, 2008.
English language Derwent Abstract of EP 1 586 302, (2005).
English language Abstract of WO 02/076416, (2002).
English language Abstract of WO 02/076417, (2001).
English language Abstract of WO 02/076418, (2002).
English language Derwent Abstract of EP 0 770 375, (1997).
English language Derwent Abstract of JP 2-19576, (1990).
English language Derwent Abstract of JP 2526099, (1996).
English language Derwent Abstract of JP 5-163124, (1993).
French Search Report for FR 05/53402, for U.S. Appl. No. 11/594,957, dated Aug. 29, 2006.
French Search Report for FR 05/53403 corresponding to U.S. Appl. No. 11/594,967, dated Jul. 24, 2006.
French Search Report for FR 07/54947 corresponding to U.S. Appl. No. 12/149,872, dated Dec. 17, 2007.
French Search Report for FR 07/54948 corresponding to U.S. Appl. No. 12/149,871, dated Dec. 13, 2007.
Fujito, H. et al., "Reaction of Pyrisnium and Isoquinolinium N-imines with Ketenethioacetals", Heterocycles 6(4): 1977, pp. 379-382.
Heyman, M. et al., "An Efficient Synthesis of Bicyclic Hydrazines and Azo Alkanes", Tetrahedron Letters 14(30): 1973, pp. 2859-2862.
Hudlicky, M., Reductions in Organic Chemistry, Ellis Horwood Limited, Chichester, England, 1983, pp. 1-13, 22-31.
Kharasch, N. et al, "Derivatives of Sulfenic Acids V. 1-Fluorenone Sulfir Coupounds", J. Am. Chem. Soc. 73: 1951, pp. 3240-3244.
Lingens, F. et al., "Uber die Umsetzung Natulich Vorkommender Pyrimidinbasen mit Hydrazin und Methylsubstituierten Hydrazinen", Justus Liebigs Ann. Chem. 686: 1965, pp. 134-145.
Magnien, E. et al., "A Re-examination of Limitations of the Hofmann Reaction", J. Org. Chem. 23: 1958, pp. 2029-2032.
March, J., Advanced Organic Chemistry, 3rd Edition, Wiley-lnterscience, New York, USA, 1985, pp. 1048-1051, & 1093-1120.
Notice of Allowance mailed Jan. 12, 2009, in co-pending U.S. Appl. No. 11/594,957.
Notice of Allowance mailed Jan. 21, 2009, in co-pending U.S. Appl. No. 12/149,872.
Notice of Allowance mailed Oct. 7, 2008, in co-pending U.S. Appl. No. 12/149,872.
Office Action mailed Feb. 5, 2009, in co-pending U.S. Appl. No. 11/594,967.
Office Action mailed Jun. 30, 2008, in co-pending U.S. Appl. No. 11/594,957.
Office Action mailed Jun. 30, 2008, in co-pending U.S. Appl. No. 11/594,967.
Stenzl, H. et al., "Zur Kenntnis der 3-Amino-pyrazolone-(5)", Helvetica Chimica Acta 33(5): 1950, pp. 1183-1194.
STIC Search Report dated Apr. 9, 2008, for U.S. Appl. No. 11/594,957.
STIC Search Report dated Apr. 9, 2008, for U.S. Appl. No. 11/594,967.
STIC Search Report dated Sep. 9, 2008, for U.S. Appl. No. 12/149,872.
English language Derwent Abstract of DE 195 43 988, (1997).
English language Derwent Abstract of DE 23 59 399, (1975).
English language Derwent Abstract of DE 38 43 892, (1990).
English language Derwent Abstract of DE 41 33 957, (1993).
English language Derwent Abstract of FR 2 822 689, (2002).
English language Derwent Abstract of FR 2 822 690, (2002).
English language Derwent Abstract of FR 2 822 691, (2002).
English language Derwent Abstract of FR 2 822 692, (2002).
Notice of Allowance mailed Apr. 28, 2009, in co-pending U.S. Appl. No. 11/594,957.
Notice of Allowance mailed Apr. 30, 2009, in co-pending U.S. Appl. No. 12/149,872.

* cited by examiner

METHOD OF COLORING KERATINOUS FIBERS COMPRISING APPLICATION OF AT LEAST ONE AMINOPYRAZOLOPYRIDINE OXIDATION BASE IN THE ABSENCE OF CHEMICAL OXIDIZING AGENTS

This application claims benefit of U.S. Provisional Application No. 60/924,851, filed Jun. 1, 2007, the contents of which are incorporated herein by reference. This application also claims benefit of priority under 35 U.S.C. § 119 to French Patent Application No. FR 0754948, filed May 9, 2007, the contents of which are also incorporated herein by reference.

Disclosed herein are methods for coloring keratinous fibers comprising applying a composition comprising at least one aminopyrazolopyridine base.

It is known to color keratinous fibers, for example human hair, with dyeing compositions comprising oxidation dye precursors, which may be known as oxidation bases, such as ortho- and para-phenylenediamines, ortho- and para-aminophenols, and heterocyclic compounds. These oxidation bases are colorless or weakly-colored compounds which, in combination with oxidizing agents, can give rise to, by an oxidative coupling process, to colored and coloring compounds.

It is also known to vary the shades obtained with these oxidation bases by combining them with couplers and/or coloring modifiers, the latter being chosen for example from aromatic meta-diamines, meta-aminophenols, meta-diphenols, and certain heterocyclic compounds, such as indole compounds.

The variety of the compounds which may be used as oxidation bases and couplers makes it possible to obtain a rich palette of colors.

The "permanent" coloring obtained by use of these oxidation dyes furthermore should satisfy a certain number of requirements. For example, it should not present toxicological challenges, it should make it possible to obtain shades within the desired intensity, and it should perform well in the face of external forces, such as light, bad weather, washing, permanent waving, perspiration, and rubbing.

The dyes should also make it possible to cover white hair and, additionally, be as non-selective as possible, that is to say, make it possible to obtain the smallest possible differences in coloring along the same keratinous fiber, which may be differentially sensitized (for example, damaged) along the length between its tip and its root.

It is known to use aminopyrazolopyridine oxidation bases for coloring keratinous fibers in the presence of an oxidizing agent, such as hydrogen peroxide, for example as described in Patent Application FR 2 801 308. These bases make it possible to obtain varied shades.

It is desirable to find hair coloring methods which exhibit dyeing properties that are improved in terms of coloring effect and resistance to external forces.

Thus, disclosed herein are methods for coloring keratinous fibers comprising applying to the keratinous fibers a dyeing composition comprising, in a medium appropriate for dyeing, at least one aminopyrazolopyridine oxidation base chosen from compounds of formula (I) and compounds of formula (II):

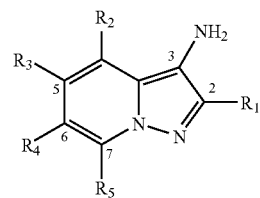

wherein:
$R_1$, $R_2$, $R_3$, $R_4$ and $R_5$, are, independently of one another, chosen from hydrogen atoms; halogen atoms; —$NHSO_3H$ radicals; hydroxyl radicals; ($C_1$-$C_4$)alkyl radicals; ($C_1$-$C_4$)alkoxy radicals; ($C_1$-$C_4$)alkylthio radicals; mono($C_1$-$C_4$)alkylamino radicals; di($C_1$-$C_4$)alkylamino radicals in which the two alkyl groups may optionally, jointly with the nitrogen atom to which they are bonded, form a ring which may be interrupted by at least one heteroatom chosen from nitrogen, oxygen, and sulfur atoms; heterocycles; nitro radicals; phenyl radicals; carbonyl radicals; ($C_1$-$C_4$)alkoxycarbonyl radicals; carboxamido radicals; cyano radicals; amino radicals; sulfonyl radicals; —$CO_2H$ radicals; —$SO_3H$ radicals; —$PO_3H_2$ radicals; —$PO_4H_2$ radicals; and groups of formula:

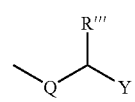

wherein R''' is chosen from oxygen atoms and nitrogen atoms, Q is chosen from oxygen atoms, NH groups, and NH($C_1$-$C_4$) alkyl groups, and Y is chosen from hydroxyl, amino, $C_1$-$C_4$ alkyl, ($C_1$-$C_4$)alkoxy, ($C_1$-$C_4$)alkylamino, and di($C_1$-$C_4$) alkylamino radicals;

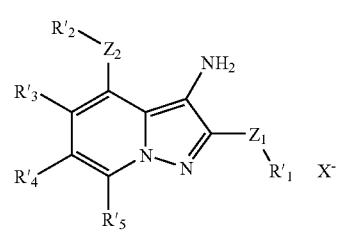

wherein:
$R'_1$ and $R'_2$ are, independently of one another, chosen from:
hydrogen atoms,
optionally substituted ($C_1$-$C_{10}$)alkyl radicals, optionally interrupted by at least one heteroatom chosen from O, N, Si, and S, and optionally interrupted by at least one group chosen from SO and $SO_2$,
halogen atoms,
—$SO_3H$ radicals,
substituted and unsubstituted, saturated, unsaturated, and aromatic 5- to 8-membered rings, optionally comprising at least one heteroatom chosen from N, O, and S, and optionally comprising at least one group chosen from $SO_2$ and —CO—, it being understood that the ring may be cationic and/or substituted by a cationic radical, —$N^+R_{17}R_{18}R_{19}$ groups, wherein $R_{17}$, $R_{18}$ and $R_{19}$ are, independently of one another, chosen from linear and branched ($C_1$-$C_5$)alkyls, optionally substituted by at least one hydroxyl group, $Z_1$ and $Z_2$ are, independently of one another, chosen from:
simple covalent bonds,
divalent radicals chosen from:
—O($CH_2$)$_p$— radicals, wherein p is an integer ranging from 0 to 6,
—$NR'_6(CH_2)_q(C_6H_4)_t$— radicals, wherein q is an integer ranging from 0 to 6, t is chosen from 0 and 1, and $R'_6$ is chosen from hydrogen atoms and ($C_1$-$C_6$)alkyl radicals optionally substituted by at least one hydroxyl group, when $R'_1$ is a methyl radical, $Z_1$ may also be chosen from divalent —S—, —SO— and —$SO_2$— radicals, when $Z_1$ is a covalent bond, $R'_1$ may also be chosen from:
optionally substituted ($C_1$-$C_6$)alkylcarbonyl radicals,
—O—CO—R, —CO—O—R, —NR—CO—R', and —CO—NRR' radicals, wherein R and R' are, independently of one another, chosen from hydrogen atoms and optionally substituted ($C_1$-$C_6$)alkyl radicals, when $Z_2$ is a covalent bond, $R_{12}$ may also be chosen from:
optionally substituted ($C_1$-$C_6$)alkylcarbonyl radicals,
—O—CO—R, —CO—O—R, —NR—CO—R', and —CO—NRR' radicals, wherein R and R' are, independently of one another, chosen from hydrogen atoms and optionally substituted ($C_1$-$C_6$)alkyl radicals, $R'_3$, $R'_4$ and $R'_5$, are, independently of one another, chosen from:
hydrogen atoms,
hydroxyl radicals,
($C_1$-$C_6$)alkoxy radicals,
($C_1$-$C_6$)alkylthio radicals,
amino radicals,
monoalkylamino radicals,
($C_1$-$C_6$)dialkylamino radicals in which the alkyl radicals may form, with the nitrogen atom to which they are attached, a saturated or unsaturated, aromatic or non-aromatic, 5- to 8-membered heterocycle which may include at least one heteroatom chosen from N, O, and S, and at least one group chosen from $SO_2$ and CO, it being understood that the heterocycle may be cationic and/or substituted by a cationic radical,
optionally substituted ($C_1$-$C_6$)alkylcarbonyl radicals,
—O—CO—R, —CO—O—R, NR—CO—R' and —CO—NRR' radicals, wherein R and R' are as defined above,
halogen atoms,
—$NHSO_3H$ radicals,
optionally substituted ($C_1$-$C_4$)alkyl radicals,
saturated, unsaturated, and aromatic rings, and optionally substituted carbon rings,
wherein it is understood that $R'_3$, $R'_4$, and $R'_5$ may form, in pairs, a saturated or unsaturated ring, $X^-$ is chosen from electronegative ions or groups of ions which make it possible for the compound of formula (II) to be electronegative,
wherein it is understood that at least one of the groups $R'_1$ and $R'_2$ is chosen from cationic radicals;
with the proviso that the method is performed without the addition of a chemical oxidizing agent.

As used herein, "chemical oxidizing agent" is understood to mean any oxidizing chemical compound, other than atmospheric oxygen, liquid or solid at a temperature of 25° C. and at atmospheric pressure ($10^5$ Pa), added to the dyeing composition.

According to one aspect of the present disclosure, the dyeing compositions disclosed herein are suitable for use in the methods for coloring keratinous fibers disclosed herein and can make it possible to obtain a coloring effect with varied, powerful, attractive, and not very selective shades which is highly resistant to the various attacks to which hair may be subjected, such as shampoos, light, sweat, and permanent deformations. According to another aspect of the present disclosure, the methods for coloring keratinous fibers can make it possible to obtain a powerful and varied coloring in the absence of chemical oxidizing agents, which can make it possible to obtain resistant colorings with little or substantially no resulting damage to the keratinous fibers.

Indeed, the inventors have discovered, surprisingly, that dyeing compositions comprising pyrazolopyridines according to the present disclosure can make it possible to obtain intense coloring of the hair without the use of hydrogen peroxide or other oxidizing agents, not including atmospheric oxygen.

As used herein, the limits delimiting a range of values are included in this range, unless otherwise indicated.

For the purposes of the present disclosure, and unless otherwise indicated, the term "alkyl" used for the alkyl radicals and for the groups comprising an alkyl part is understood to mean a linear or branched carbon chain comprising from 1 to 4 carbon atoms which may be unsubstituted or substituted by at least one heterocycle and/or by at least one phenyl group and/or by at least one group chosen from halogen atoms, for example chlorine, bromine, iodine, and fluorine atoms, hydroxyl, alkoxy, amino, carbonyl, carboxamido, sulfonyl, —$CO_2H$, —$SO_3H$, —$PO_3H_2$, —$PO_4H_2$, —$NHSO_3H$, sulfonamido, mono($C_1$-$C_4$)alkylamino, tri($C_1$-$C_4$)alkylammonium radicals, and di($C_1$-$C_4$)alkylamino radicals in which the two alkyl groups can form, together with the nitrogen atom of the said di($C_1$-$C_4$)alkylamino group to which they are bonded, a ring which can be interrupted by at least one heteroatom chosen from nitrogen, oxygen, and sulfur atoms.

For the purposes of the present disclosure, and unless otherwise indicated, the term "alkoxy" used for alkoxy radicals and for the groups comprising an alkoxy part is understood to mean a linear or branched O-carbon chain comprising from 1 to 4 carbon atoms which may be unsubstituted or substituted by at least one group chosen from heterocycles; halogen atoms, for example chlorine, bromine, iodine, and fluorine atoms; hydroxyl, amino, carbonyl, carboxamido, sulfonyl, —$CO_2H$, —$SO_3H$, —$PO_3H_2$, —$PO_4H_2$, —$NHSO_3H$, sulfonamido, mono($C_1$-$C_4$)alkylamino, tri($C_1$-$C_4$)alkylammonium radicals, and di($C_1$-$C_4$)alkylamino radicals in which the two alkyl groups can form, together with the nitrogen atom of the said di($C_1$-$C_4$)alkylamino group to which they are bonded, a ring which may be interrupted by at least one heteroatom chosen from nitrogen, oxygen, and sulfur atoms.

For the purposes of the present disclosure, and unless otherwise indicated, the term "heterocycle" is understood to mean a 5-, 6-, 7-, or 8-membered aromatic or non-aromatic ring comprising from 1 to 3 heteroatoms chosen from nitrogen, sulfur, and oxygen atoms. These heterocycles may be fused to at least one other heterocycle and/or to at least one phenyl group. They may also be substituted by at least one substituent chosen from halogen atoms, for example chlorine, bromine, iodine, and fluorine atoms; ($C_1$-$C_4$)alkyl radicals; ($C_1$-$C_4$)alkoxy radicals; hydroxyl radicals; amino radicals;

($C_1$-$C_4$)alkylamino radicals; and di($C_1$-$C_4$)alkylamino radicals in which the two alkyl groups can form, together with the nitrogen atom of the said di($C_1$-$C_4$)alkylamino group to which they are bonded, a ring which may be interrupted by at least one heteroatom chosen from nitrogen, oxygen, and sulfur atoms. In addition, these heterocycles may be quaternized by ($C_1$-$C_4$)alkyl radicals.

As optionally-fused heterocycles described above, non-limiting examples include: thiadiazole, triazole, isoxazole, oxazole, azaphosphole, thiazole, isothiazole, imidazole, pyrazole, triazine, thiazine, pyrazine, pyridazine, pyrimidine, pyridine, diazepine, oxazepine, benzotriazole, benzoxazole, benzimidazole, benzothiazole, morpholine, piperidine, piperazine, azetidine, pyrrolidine, aziridine, 3-(2-hydroxyethyl) benzothiazol-3-ium, and 1-(2-hydroxyethyl)pyridinium.

For the purposes of the present disclosure, and unless otherwise indicated, the term "phenyl" is understood to mean a phenyl radical which may be unsubstituted or substituted by at least one substituent chosen from cyano, carbonyl, carboxamido, sulfonyl, —$CO_2H$, —$SO_3H$, —$PO_3H_2$, —$PO_4H_2$, hydroxyl, amino, mono($C_1$-$C_4$)alkylamino, and di($C_1$-$C_4$) alkylamino radicals, it being possible, in the case of di($C_1$-$C_4$)alkylamino radicals, for the two alkyl groups to form, together with the nitrogen atom of the said di($C_1$-$C_4$)alkylamino group to which they are bonded, a ring which may be interrupted by at least one heteroatom chosen from nitrogen, oxygen, and sulfur atoms.

As

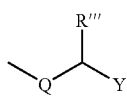

groups described above, non-limiting examples include: acetamide, dimethylurea, O-methylcarbamate, methylcarbonate, N,N-dimethylcarbamate groups, and esters thereof.

In one embodiment of the present disclosure, as compounds of the above formula (I), non-limiting examples include 3-aminopyrazolo[1,5-a]pyridines of subformula (Ia), their addition salts with an acid, and their addition salts with a base:

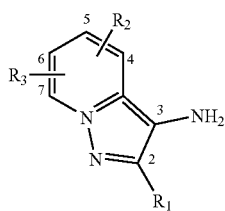

(Ia)

wherein:
$R_1$, $R_2$, and $R_3$ are, independently of one another, chosen from hydrogen atoms; halogen atoms; hydroxyl radicals; ($C_1$-$C_4$)alkyl radicals; ($C_1$-$C_4$)alkylthio radicals; ($C_1$-$C_4$)alkoxy radicals; —$NHSO_3H$ radicals; amino radicals; ($C_{1-4}$)alkylamino radicals; di($C_1$-$C_4$)alkylamino radicals wherein the two alkyl groups can, jointly with the nitrogen atom to which they are bonded, form a ring which may be interrupted by at least one heteroatom chosen from nitrogen, oxygen, and sulfur atoms; heterocycles as defined above; sulfonamido radicals; carbonyl radicals; ($C_1$-$C_4$)alkoxycarbonyl radicals; carboxamido radicals; and groups of formula:

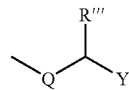

wherein R''' is chosen from oxygen and nitrogen atoms, Q is chosen from oxygen atoms, NH groups, and NH($C_1$-$C_4$)alkyl groups, and Y is chosen from hydroxyl, amino, ($C_1$-$C_4$)alkyl, ($C_1$-$C_4$)alkoxy, ($C_1$-$C_4$)alkylamino, and di($C_1$-$C_4$)alkylamino radicals.

Among 3-aminopyrazolo[1,5-a]pyridines of formula (I) which can be used as the at least one oxidation base in dyeing compositions for the method according to the present disclosure, non-limiting examples include:
pyrazolo[1,5-a]pyridin-3-ylamine;
2-acetylaminopyrazolo[1,5-a]pyridin-3-ylamine;
2-(morpholin-4-yl)pyrazolo[1,5-a]pyridin-3-ylamine;
3-aminopyrazolo[1,5-a]pyridine-2-carboxylic acid;
2-methoxypyrazolo[1,5-a]pyridin-3-ylamine;
(3-aminopyrazolo[1,5-a]pyridin-7-yl)methanol;
2-(3-aminopyrazolo[1,5-a]pyridin-5-yl)ethanol;
2-(3-aminopyrazolo[1,5-a]pyridin-7-yl)ethanol;
(3-aminopyrazolo[1,5-a]pyridin-2-yl)methanol;
3,6-diaminopyrazolo[1,5-a]pyridine;
3,4-diaminopyrazolo[1,5-a]pyridine;
pyrazolo[1,5-a]pyridine-3,7-diamine;
7-(morpholin-4-yl)pyrazolo[1,5-a]pyridin-3-ylamine;
pyrazolo[1,5-a]pyridine-3,5-diamine;
5-(morpholin-4-yl)pyrazolo[1,5-a]pyridin-3-ylamine;
2-[(3-aminopyrazolo[1,5-a]pyridin-5-yl)(2-hydroxyethyl)amino]ethanol;
2-[(3-aminopyrazolo[1,5-a]pyridin-7-yl)(2-hydroxyethyl)amino]ethanol;
3-aminopyrazolo[1,5-a]pyridin-5-ol;
3-aminopyrazolo[1,5-a]pyridin-4-ol;
3-aminopyrazolo[1,5-a]pyridin-6-ol;
3-aminopyrazolo[1,5-a]pyridin-7-ol;
2-methoxy-6,7-dimethylpyrazolo[1,5-a]pyridin-3-amine;
2-[(3-aminopyrazolo[1,5-a]pyridin-2-yl)oxy]-ethanol;
4-ethyl-2-methoxy-7-methylpyrazolo[1,5-a]pyridin-3-amine hydrochloride;
1-(3-aminopyrazolo[1,5-a]pyridin-2-yl)pyrrolidin-3-ol;
2,2'-[(3-aminopyrazolo[1,5-a]pyridin-2-yl)imino]diethanol;
2-[(3-aminopyrazolo[1,5-a]pyridin-2-yl)amino]-ethanol;
N2-(2-(pyridin-3-yl)ethyl)pyrazolo[1,5-a]pyridine-2,3-diamine;

and their addition salts with an acid or with a base.

A number of 3-aminopyrazolo[1,5-a]pyridines of formula (I) are known in the pharmaceutical field, for example, those described in U.S. Pat. No. 5,457,200. These compounds can be prepared according to synthetic methods described, for example, in U.S. Pat. No. 5,457,200.

For the purposes of the present disclosure, and unless otherwise indicated, the terms "cationic ring" and "cationic heterocycle" are understood to mean a ring comprising at least one quaternary ammonium group.

As —$N^+R_{17}R_{18}R_{19}$ radicals, non-limiting examples include: trimethylammonium, triethylammonium, dimethylethylammonium, diethylmethylammonium, diisopropylmethylammonium, diethylpropylammonium, (β-hydroxyethyl)diethylammonium, di(β-hydroxyethyl)methylammonium, and tri(β-hydroxyethyl)ammonium radicals.

As cationic heterocycles, non-limiting examples include: imidazoliums, pyridiniums, piperaziniums, pyrrolidiniums, morpholiniums, pyrimidiniums, thiazoliums, benzimidazoliums, benzothiazoliums, oxazoliums, benzotriazoliums, pyrazoliums, triazoliums, and benzoxazoliums.

According to the present disclosure, compounds of formula (II) may optionally be salified with strong inorganic acids, such as, for example, HCl, HBr, $H_1$, $H_2SO_4$, and $H_3PO_4$, or organic acids, such as, for example, acetic acid, lactic acid, tartaric acid, citric acid, succinic acid, benzenesulfonic acid, para-toluenesulfonic acid, formic acid, and methanesulfonic acid.

According to the present disclosure, compounds of formula (II) comprising anionic groups, for example —$CO_2H$, —$SO_3H$, —$PO_3H_2$ and/or —$PO_4H_2$ groups, may optionally be salified by alkali metal or alkaline earth metal hydroxides, such as sodium hydroxide or potassium hydroxide, by aqueous ammonia, or by organic amines.

In one embodiment of the present disclosure, compounds of formula (II) may be in the form of solvates, for example a hydrate or a solvate of a linear or branched alcohol, such as ethanol and isopropanol.

For the purposes of the present disclosure, and unless otherwise indicated, the term "derivative of formula (II)" is understood to comprise all mesomeric and isomeric forms of compounds of formula (II).

As derivatives of formula (II), non-limiting examples include the following compounds, wherein $X^-$ is as defined above:

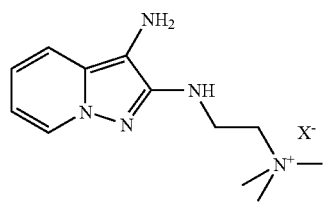

[2-(3-Aminopyrazolo[1,5-a]pyridin-2-ylamino)ethyl]trimethylammonium salt

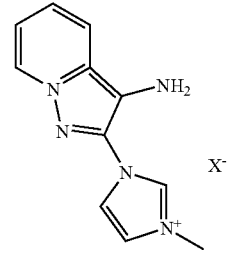

3-(3-Aminopyrazolo[1,5-a]pyridin-2-yl)-1-methyl-3H-imidaol-1-ium salt

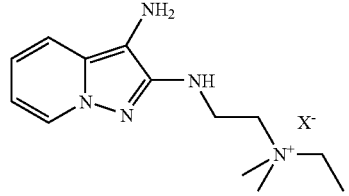

[2-(3-Aminopyrazolo[1,5-a]pyridin-2-ylamino)ethyl]ethyldimethylammonium salt

-continued

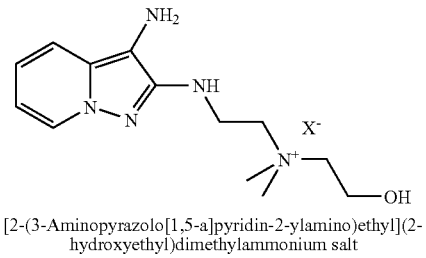

[2-(3-Aminopyrazolo[1,5-a]pyridin-2-ylamino)ethyl](2-hydroxyethyl)dimethylammonium salt

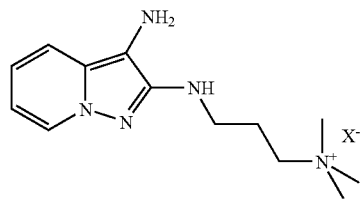

[3-(3-Aminopyrazolo[1,5-a]pyridin-2-ylamino)propyl]trimethylammonium salt

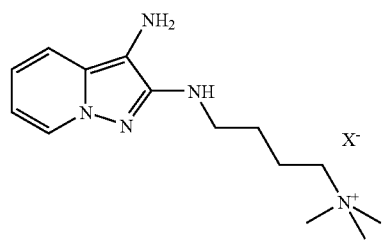

[4-(3-Aminopyrazolo[1,5-a]pyridin-2-ylamino)butyl]-trimethylammonium salt

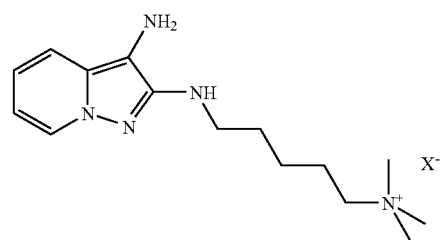

[5-(3-Aminopyrazolo[1,5-a]pyridin-2-ylamino)pentyl]trimethylammonium salt

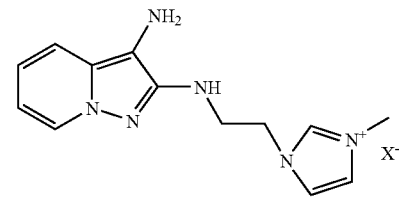

3-[2-(3-Aminopyrazolo[1,5-a]pyridin-2-ylamino)ethyl]-1-methyl-3H-imidazol-1-ium salt

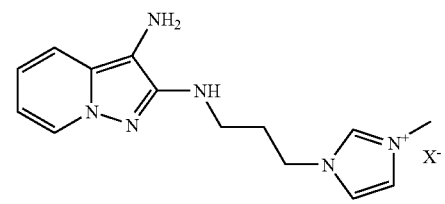

3-[3-(3-Aminopyrazolo[1,5-a]pyridin-2-ylamino)propyl]-1-methyl-3H-imidazol-1-ium salt

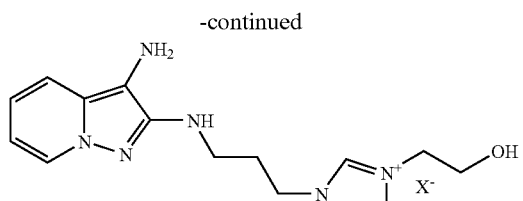

3-[3-(3-Aminopyrazolo[1,5-a]pyridin-2-ylamino)propyl]-
1-(2-hydroxyethyl)-3H-imidazol-1-ium salt

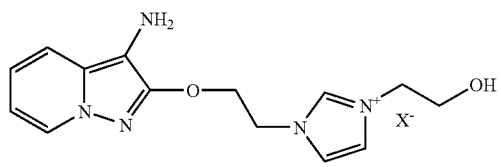

3-[2-(3-Aminopyrazolo[1,5-a]pyridin-2-yloxy)ethyl]-
1-(2-hydroxyethyl)-3H-imidazol-1-ium salt

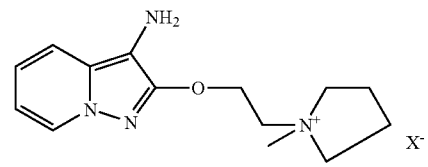

1-{2-[(3-Aminopyrazolo[1,5-a]pyridin-2-yl)oxy]ethyl}-
1-methylpyrrolidinium salt

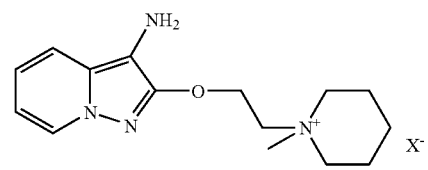

1-{2-[(3-Aminopyrazolo[1,5-a]pyridin-2-yl)oxy]ethyl}-
1-methylpiperidinium salt

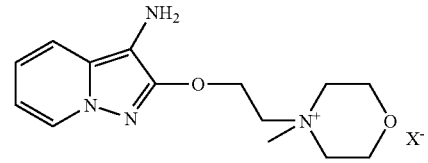

4-{2-[(3-Aminopyrazolo[1,5-a]pyridin-2-yl)oxy]ethyl}-
4-methylmorpholin-4-ium salt

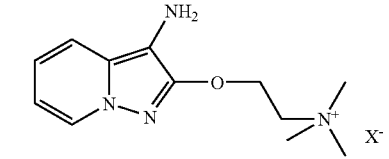

{2-[(3-Aminopyrazolo[1,5-a]pyridin-2-yl)oxy]ethyl}
trimethylammonium salt

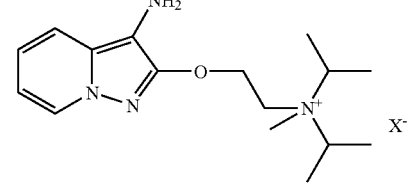

{2-[(3-Aminopyrazolo[1,5-a]pyridin-2-yl)oxy]ethyl}-
diisopropylmethylammonium salt

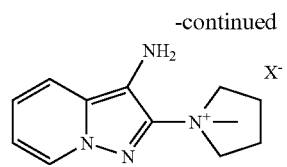

1-(3-Aminopyrazolo[1,5-a]pyridin-2-yl)-1-
methylpyrrolidinium salt

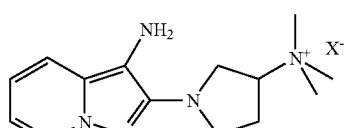

1-(3-Aminopyrazolo[1,5-a]pyridin-2-yl)pyrrolidin-
3-yl]trimethylammonium salt

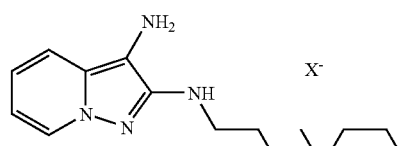

1-[3-(3-Aminopyrazolo[1,5-a]pyridin-2-ylamino)
propyl]-1-methylpiperidinium salt

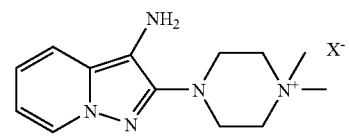

4-(3-Aminopyrazolo[1,5-a]pyridin-2-yl)-1,1-
dimethylpiperazin-1-ium salt

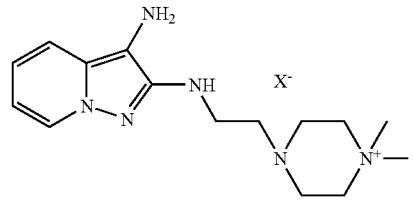

4-[2-(3-Aminopyrazolo[1,5-a]pyridin-2-ylamino)ethyl]-1,1-
dimethylpiperazin-1-ium salt

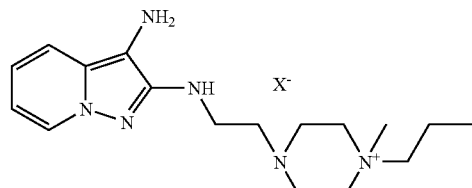

4-[2-(3-Aminopyrazolo[1,5-a]pyridin-2-ylamino)ethyl]-1-
methyl-1-propylpiperazin-1-ium salt

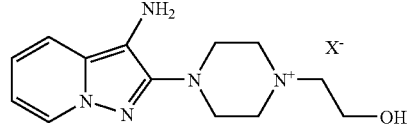

4-(3-Aminopyrazolo[1,5-a]pyridin-2-yl)-1-
(2-hydroxyethyl)piperazin-1-ium salt

-continued
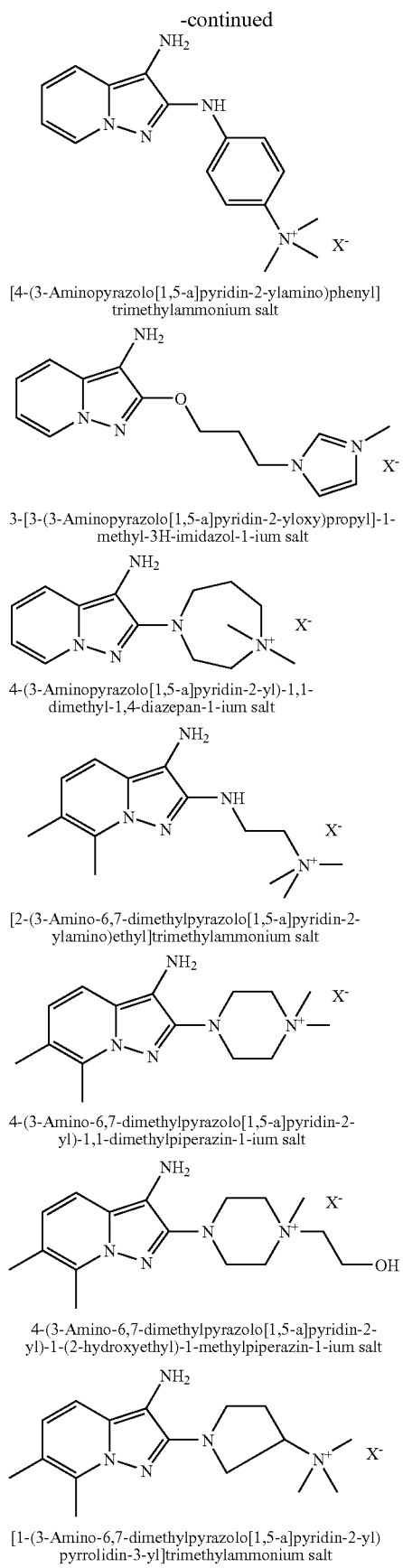
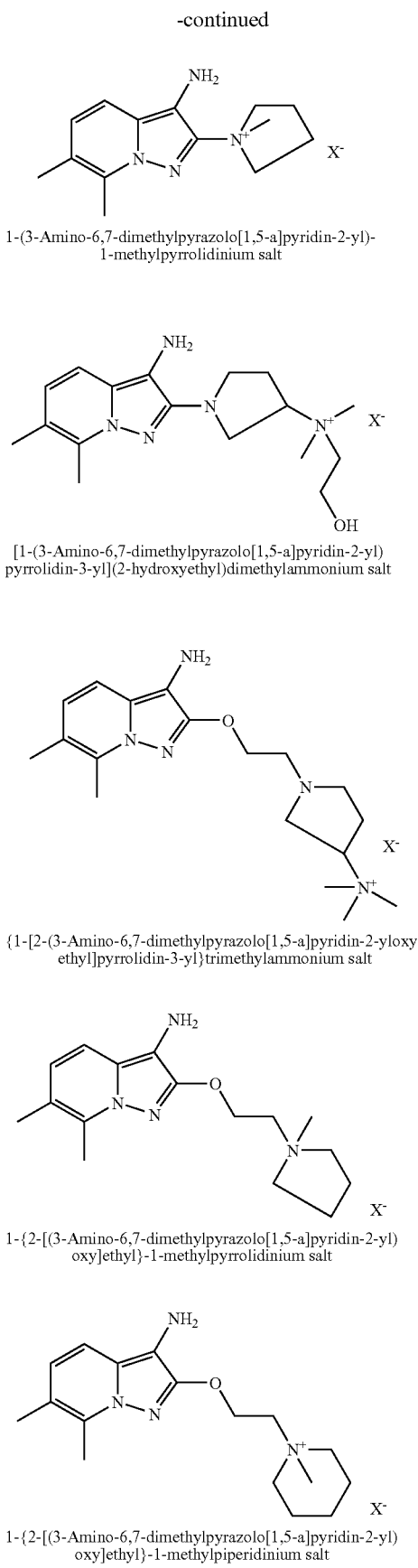

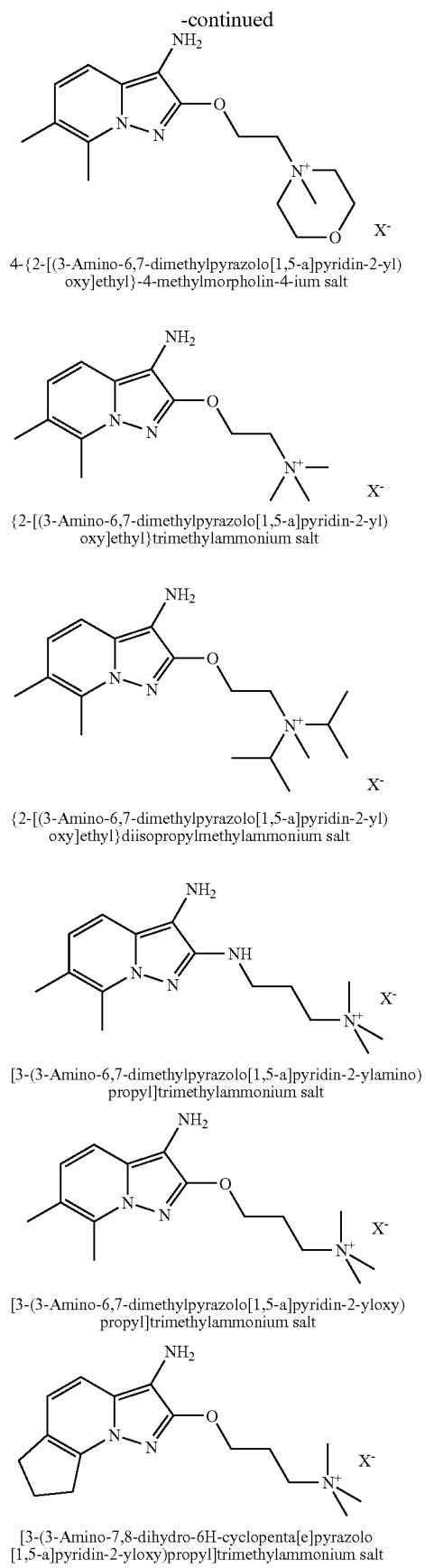
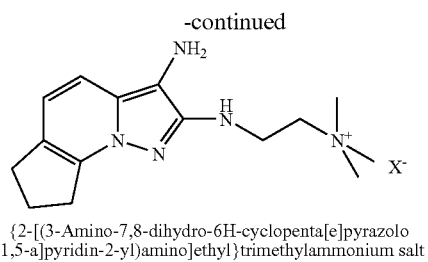

4-{2-[(3-Amino-6,7-dimethylpyrazolo[1,5-a]pyridin-2-yl)oxy]ethyl}-4-methylmorpholin-4-ium salt {2-[(3-Amino-6,7-dimethylpyrazolo[1,5-a]pyridin-2-yl)oxy]ethyl}trimethylammonium salt {2-[(3-Amino-6,7-dimethylpyrazolo[1,5-a]pyridin-2-yl)oxy]ethyl}diisopropylmethylammonium salt

[3-(3-Amino-6,7-dimethylpyrazolo[1,5-a]pyridin-2-ylamino)propyl]trimethylammonium salt

[3-(3-Amino-6,7-dimethylpyrazolo[1,5-a]pyridin-2-yloxy)propyl]trimethylammonium salt

[3-(3-Amino-7,8-dihydro-6H-cyclopenta[e]pyrazolo[1,5-a]pyridin-2-yloxy)propyl]trimethylammonium salt {2-[(3-Amino-7,8-dihydro-6H-cyclopenta[e]pyrazolo[1,5-a]pyridin-2-yl)amino]ethyl}trimethylammonium salt {3-[(3-Amino-7,8-dihydro-6H-cyclopenta[e]pyrazolo[1,5-a]pyridin-2-yl)amino]propyl}trimethylammonium salt 1-{2-[(3-Amino-7,8-dihydro-6H-cyclopenta[e]pyrazolo[1,5-a]pyridin-2-yl)amino]ethyl}-3-methyl-1H-imidazol-3-ium salt 1-{3-[(3-Amino-7,8-dihydro-6H-cyclopenta[e]pyrazolo[1,5-a]pyridin-2-yl)amino]propyl}-3-methyl-1H-imidazol-3-ium salt 1-{2-[(3-Amino-7,8-dihydro-6H-cyclopenta[e]pyrazolo[1,5-a]pyridin-2-yl)amino]ethyl}-1-methylpyrrolidinium salt 1-{2-[(3-Amino-7,8-dihydro-6H-cyclopenta[e]pyrazolo[1,5-a]pyridin-2-yl)amino]ethyl}-1-methylpiperidinium salt 4-{2-[(3-Amino-7,8-dihydro-6H-cyclopenta[e]pyrazolo[1,5-a]pyridin-2-yl)amino]ethyl}-4-methylmorpholin-4-ium salt -continued

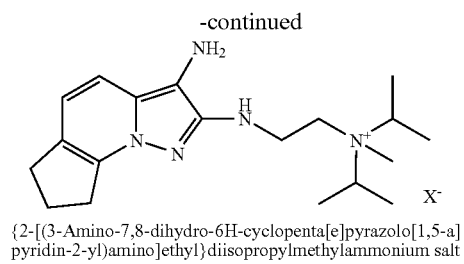

{2-[(3-Amino-7,8-dihydro-6H-cyclopenta[e]pyrazolo[1,5-a]pyridin-2-yl)amino]ethyl}diisopropylmethylammonium salt

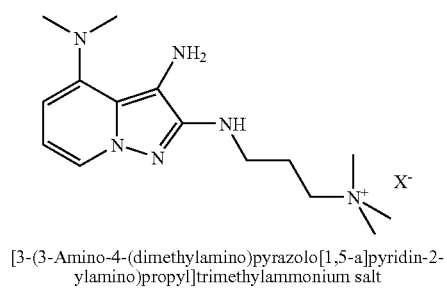

[3-(3-Amino-4-(dimethylamino)pyrazolo[1,5-a]pyridin-2-ylamino)propyl]trimethylammonium salt

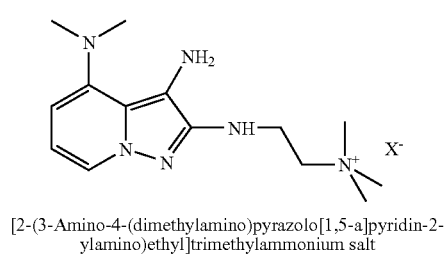

[2-(3-Amino-4-(dimethylamino)pyrazolo[1,5-a]pyridin-2-ylamino)ethyl]trimethylammonium salt

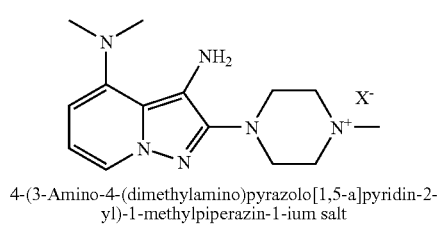

4-(3-Amino-4-(dimethylamino)pyrazolo[1,5-a]pyridin-2-yl)-1-methylpiperazin-1-ium salt

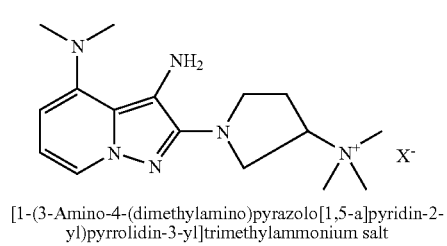

[1-(3-Amino-4-(dimethylamino)pyrazolo[1,5-a]pyridin-2-yl)pyrrolidin-3-yl]trimethylammonium salt

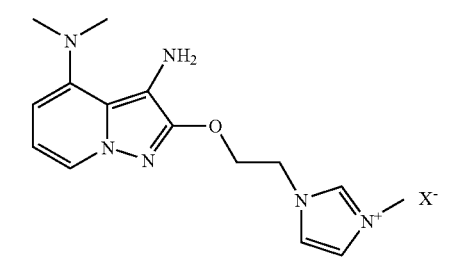

3-[2-(3-Amino-4-(dimethylamino)pyrazolo[1,5-a]pyridin-2-yloxy)ethyl]-1-methyl-3H-imidazol-1-ium salt -continued

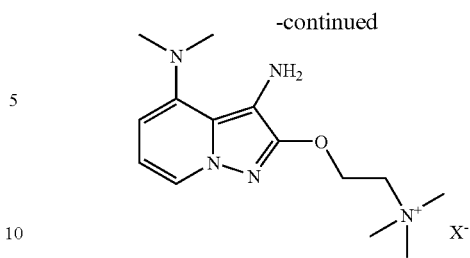

[2-(3-Amino-4-(dimethylamino)pyrazolo[1,5-a]pyridin-2-yloxy)ethyl]trimethylammonium salt

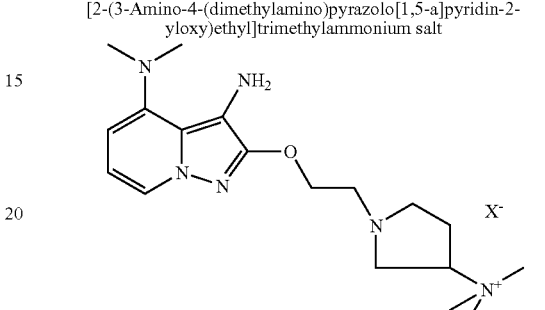

{1-[2-(3-Amino-4-(dimethylamino)pyrazolo[1,5-a]pyridin-2-yloxy)ethyl]pyrrolidin-3-yl}trimethylammonium salt

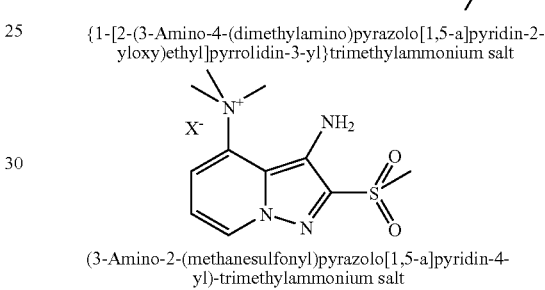

(3-Amino-2-(methanesulfonyl)pyrazolo[1,5-a]pyridin-4-yl)-trimethylammonium salt

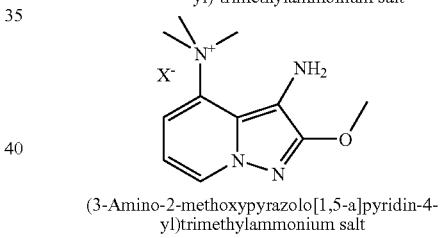

(3-Amino-2-methoxypyrazolo[1,5-a]pyridin-4-yl)trimethylammonium salt

The nature of the counter-ion is not determining with regard to the dyeing power of the compounds of formula (II).

In at least one embodiment, when $R'_1$ or $R'_2$ is a heterocycle, said heterocycle is a cationic heterocycle or a heterocycle substituted by a cationic radical. As cationic heterocycles and heterocycles substituted by cationic radicals, non-limiting examples include: imidazoles substituted by a quaternary ammonium radical, imidazoliums, piperazines substituted by a quaternary ammonium radical, piperaziniums, pyrrolidines substituted by a quaternary ammonium radical, pyrrolidiniums, diazepanes substituted by a quaternary ammonium radical, and diazepaniums.

In at least another embodiment, at least one of $R'_1$ and $R'_2$ may be chosen from —$N^+R_{17}R_{18}R_{19}$ groups wherein $R_{17}$, $R_{18}$, and $R_{19}$ are chosen from linear and branched ($C_1$-$C_5$) alkyls, optionally substituted by at least one hydroxyl group, for example trialkylammonium, tri(hydroxyalkyl)ammonium, (hydroxyalkyl)dialkylammonium, and di(hydroxyalkyl)alkylammonium groups.

The $R'_3$, $R'_4$, and $R'_5$ radicals can be, independently of one another, chosen from hydrogen atoms and optionally substituted ($C_1$-$C_4$)alkyl radicals, for example methyl, ethyl, hydroxyethyl, aminoethyl, propyl, and butyl radicals. According to at least one embodiment, R'$_3$, R'$_4$, and R'$_5$ are, independently of one another, chosen from hydrogen atoms and (C$_1$-C$_4$)alkyl radicals.

In one embodiment, R'$_4$ and R'$_5$ together form a partially saturated or unsaturated 5- or 6-membered ring, for example a cyclopentene or cyclohexene ring, which is optionally substituted.

In one embodiment, at least one compound of formula (II) may be chosen from compounds of subformula (IIa):

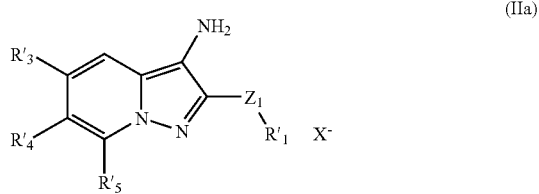

(IIa)

wherein Z$_1$, R'$_1$, R'$_3$, R'$_4$, and R'$_5$ are as defined above.

In one embodiment of subformula (IIa), Z$_1$ is chosen from covalent bonds, —NR'$_6$(CH$_2$)$_q$— radicals, and —O(CH$_2$)$_p$— radicals, and R'$_1$ is chosen from cationic radicals.

The at least one oxidation base as disclosed herein may be present in an amount ranging from 0.001 to 10% by weight, for example from 0.005 to 6% by weight, relative to the total weight of the composition.

Dyeing compositions according to the present disclosure may comprise at least one coupler. As couplers which may be used in the dyeing compositions, non-limiting examples include those conventionally used for dyeing keratinous fibers, for example meta-phenylenediamines, meta-aminophenols, meta-diphenols, naphthalene couplers, heterocyclic couplers, and addition salts thereof.

In at least one embodiment of the present disclosure, non-limiting examples from which couplers may be chosen include: 2-methyl-5-aminophenol, 5-N-(β-hydroxyethyl) amino-2-methylphenol, 6-chloro-2-methyl-5-aminophenol, 3-aminophenol, 2,4-dichloro-3-aminophenol, 5-amino-4-chloro-o-cresol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-(β-hydroxyethylamino)-3,4-methylenedioxybenzene, α-naphthol, 2-methyl-1-naphthol, 1,5-dihydroxynaphthalene, 2,7-naphthalenediol, 1-acetoxy-2-methylnaphthalene, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 2,6-dihydroxy-3-4-dimethylpyridine, 3-amino-2-methylamino-6-methoxypyridine, 1-N-(β-hydroxyethyl) amino-3,4-methylenedioxybenzene, 2,6-bis(β-hydroxyethylamino)toluene, 3-methyl-1-phenyl-5-pyrazolone, and the acid addition salts thereof.

Dyeing compositions used in the method according to the present disclosure may further comprise at least one additional oxidation base not chosen from compounds of formula (I) or (II). As additional oxidation bases not chosen from compounds of formula (I) or (II) which may be used, non-limiting examples include those conventionally used in oxidation dyeing, for example para-phenylenediamines other than those described above, bis-phenylalkylenediamines, para-aminophenols, bis-para-aminophenols, ortho-aminophenols, heterocyclic bases not chosen from compounds of formula (I) or (II), and the addition salts thereof.

As para-phenylenediamines, non-limiting examples include: para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-para-phenylene-diamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl, β-hydroxyethyl)-para-phenylenediamine, N-(β, γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 4-aminophenylpyrrolidine, 2-thienyl-para-phenylenediamine, 2-(β-hydroxyethylamino)-5-aminotoluene, 3-hydroxy-1-(4'-aminophenyl)pyrrolidine, and the acid addition salts thereof.

In at least one embodiment of the present disclosure, the at least one additional oxidation base may be chosen from para-phenylenediamine, para-toluenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-(β-acetylaminoethyloxy)-para-phenylenediamine, and the acid addition salts thereof.

As bisphenylalkylenediamines, non-limiting examples include: N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylene-diamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,6-dioxaoctane and the acid addition salts thereof.

As para-aminophenols, non-limiting examples include: para-aminophenol, 4-amino-3-methylphenol, 4-amino-3-fluorophenol, 4-amino-3-(hydroxymethyl)phenol, 4-amino-2-methylphenol, 4-amino-2-(hydroxymethyl)phenol, 4-amino-2-(methoxy-methyl)phenol, 4-amino-2-(aminomethyl)phenol, 4-amino-2-((β-hydroxyethyl)amino-methyl) phenol, 4-amino-2-fluorophenol, and the acid addition salts thereof.

As ortho-aminophenols, non-limiting examples include: 2-aminophenol, 2-amino-5-methylphenol, 2-amino-6-methylphenol, 5-acetamido-2-aminophenol, and the acid addition salts thereof.

As heterocyclic bases, non-limiting examples include: pyridine derivatives, pyrimidine derivatives, and pyrazole derivatives.

Non-limiting examples from which the pyridine derivatives may be chosen include the compounds disclosed, for example, in Patents GB 1 026 978 and GB 1 153 196, such as 2,5-diaminopyridine, 2-[(4-methoxyphenyl)amino]-3-aminopyridine, 2,3-diamino-6-methoxypyridine, 2-[(β-methoxyethyl)amino]-3-amino-6-methoxypyridine, 3,4-diaminopyridine, and the acid addition salts thereof.

Non-limiting examples from which the pyrimidine derivatives may be chosen include the compounds disclosed, for example, in Patents DE 2 359 399; JP 88-169571; JP 05-63124; EP 0 770 375 and PCT Publication WO 96/15765, such as 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and pyrazolopyrimidine derivatives, for example those mentioned in Patent Application FR-A-2 750 048, such as pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidine-5-ol; 2-(3-amino-pyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethyl-pyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-(imidazolylpropylamino)pyrazolo[1,5-a]pyrimidine, the acid addition salts thereof, and the tautomeric forms thereof, when a tautomeric equilibrium exists.

Non-limiting examples from which the pyrazole derivatives may be chosen include the compounds disclosed in Patents DE 3 843 892 and DE 4 133 957, PCT Publications WO 94/08969, WO 94/08970, and Patent Applications FR-A-2 733 749 and DE 195 43 988, such as 4,5-diamino-1-methylpyrazole, 4,5-diamino-1-(β-hydroxy-ethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-(tert-butyl)-1-methylpyrazole, 4,5-diamino-1-(tert-butyl)-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-(hydroxymethyl)pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-(methylamino)pyrazole, 3,5-diamino-4-(β-hydroxyethyl)amino-1-methylpyrazole, and the acid addition salts thereof.

Non-limiting examples from which heterocyclic bases may be chosen include the diaminopyrazolinones disclosed in Patent Application FR 2 886 137, for example 2,3-diamino-6,7-dihydro-1H,5H-pyrazol-1-one and its salts.

As addition salts of oxidation bases and/or couplers which may be used in the context of the present disclosure, non-limiting examples include acid addition salts, for example hydrochlorides, hydrobromides, sulfates, citrates, succinates, tartrates, lactates, tosylates, benzenesulfonates, phosphates, and acetates, and base addition salts, for example sodium hydroxide, potassium hydroxide, aqueous ammonia, amines, and alkanolamines.

Dyeing compositions used in the methods according to the present disclosure may further comprise at least one direct dye, which may be chosen from nonionic, anionic, and cationic dyes. As direct dyes, non-limiting examples include nitrobenzene dyes, azo direct dyes, and methine direct dyes.

The medium appropriate for dyeing, which may alternatively be referred to as the dyeing vehicle, can be an aqueous medium comprising water or a mixture of water and at least one organic solvent, for example to improve solubility of compounds which would not be sufficiently soluble in pure water. As organic solvents, non-limiting examples include: lower $C_1$-$C_4$ alkanols, such as ethanol and isopropanol; polyols and polyol ethers, such as 2-butoxyethanol, propylene glycol, propylene glycol monomethyl ether, diethylene glycol monoethyl ether and diethylene glycol monomethyl ether; aromatic alcohols, such as benzyl alcohol and phenoxyethanol; and mixtures thereof.

The optional organic solvents may be present in amounts ranging from 1 to 40% by weight, for example from 5 to 30% by weight, relative to the total weight of the dyeing composition.

The dyeing compositions used in the methods in accordance with the present disclosure may also comprise at least one adjuvant, for example adjuvants chosen from those conventionally used in compositions for dyeing the hair, such as anionic, cationic, nonionic, amphoteric, and zwitterionic surfactants and mixtures thereof; anionic, cationic, nonionic, amphoteric, and zwitterionic polymers and mixtures thereof; inorganic and organic thickening agents, for example anionic, cationic, nonionic, and amphoteric polymeric associative thickeners; antioxidants; penetration agents; sequestering agents; fragrances; buffers; dispersing agents; conditioning agents, such as, for example, volatile and non-volatile, modified and unmodified silicones; film-forming agents; ceramides; preservatives; and opacifying agents.

The above adjuvants may be present in dyeing compositions according to the present disclosure in an amount ranging from 0.01 to 20% by weight, relative to the total weight of the composition.

A person skilled in the art will take care to choose the optional additional compound or compounds so that the beneficial properties intrinsically associated with the methods of coloring keratinous fibers according to the present disclosure are not, or not substantially, detrimentally affected by the envisaged addition or additions.

Dyeing compositions used in the methods in accordance with the present disclosure can have a pH ranging from 3 to 12, for example from ranging from 5 to 11. The pH of dyeing compositions according to the present disclosure may be adjusted to a particular value via conventional buffering systems and/or by addition of acidifying or basifying agents such as those commonly used in compositions for dyeing keratinous fibers. In one embodiment, the medium appropriate for dyeing is basic.

As acidifying agents, non-limiting examples include: inorganic and organic acids, such as hydrochloric acid, orthophosphoric acid, sulfuric acid, carboxylic acids, such as acetic acid, tartaric acid, citric acid, and lactic acid, and sulfonic acids.

As basifying agents, non-limiting examples include: aqueous ammonia, alkaline carbonates, alkanolamines, such as mono-, di-, and triethanolamines and their derivatives, sodium hydroxide, potassium hydroxide, and compounds of formula (III):

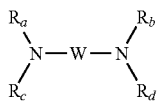

(III)

wherein W is a propylene residue optionally substituted by a hydroxyl group or a ($C_1$-$C_4$)alkyl radical, and $R_a$, $R_b$, $R_c$, and $R_d$, are, independently of one another, chosen from hydrogen atoms, ($C_1$-$C_4$)alkyl radicals, and ($C_1$-$C_4$)hydroxyalkyl radicals.

Dyeing compositions according to the present disclosure may be provided in various forms, for example in the form of liquids, of creams, or of gels, or in any other form appropriate for use in methods of coloring keratinous fibers such as human hair.

In the method of the present disclosure, after a setting time ranging from 1 to 60 minutes, for example from 5 to 45 minutes, after application of a dyeing composition, the keratinous fibers may be rinsed, washed with shampoo, rinsed again, and then dried.

Ready-for-use dyeing compositions according to the present disclosure which are applied to keratinous fibers may be provided in various forms, such as in the form of liquids, of creams, or of gels, or in any other form appropriate for use in methods of coloring keratinous fibers such as human hair.

The methods of coloring keratinous fibers according to the present disclosure are performed in the presence of atmospheric oxygen and without the addition of chemical oxidizing agents. That is to say, the methods of coloring keratinous fibers according to the present disclosure make it possible to achieve a coloring effect in the absence of chemical oxidizing agents such as those conventionally used in the field of oxidation dyeing, for example, in the absence of hydrogen peroxide, urea hydrogen peroxide, alkali metal bromates, persalts, such as perborates and persulfates, and peracids.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The examples that follow are intended to illustrate the present disclosure without, however, being limiting in nature.

EXAMPLES

Example 1

Dyeing compositions were prepared from the medium described below and the following dyes (amounts expressed in mol unless otherwise indicated):

| In moles per 100 g of composition | B1 | B2 | C1 | C2 | C3 | C4 |
|---|---|---|---|---|---|---|
| Composition A1 | 0.005 | | | | | |
| Composition A2 | | 0.005 | | | | |
| Composition A8 | 0.0025 | | 0.0025 | | | |
| Composition A9 | 0.0025 | | | 0.0025 | | |
| Composition A10 | 0.0025 | | | | 0.0025 | |
| Composition A11 | 0.0025 | | | | | 0.0025 |
| Composition A13 | | 0.0025 | 0.0025 | | | |
| Composition A14 | | 0.0025 | | 0.0025 | | |
| Composition A15 | | 0.0025 | | | 0.0025 | |
| Composition A16 | | 0.0025 | | | | 0.0025 |

B1 = 2-[(3-Aminopyrazolo[1,5-a]pyridin-2-yl)amino]-N,N,N-trimethylethanaminium chloride hydrochloride
B2 = 2-[(3-Aminopyrazolo[1,5-a]pyridin-2-yl)oxy]ethanol hydrochloride
C1 = 1-Methyl-2-hydroxy-4-aminobenzene
C2 = 2,4-Diaminophenoxyethanol
C3 = 2-Amino-3-hydroxypyridine
C4 = 6-Hydroxyindole Medium of the Dyeing Compositions:

| | |
|---|---|
| Sodium sulfite | 0.1 g |
| Oxyethylenated sodium lauryl ether sulfate (2.2 EO) as a 30% aqueous solution | 1.0 g |
| Ethanol | 5.0 g |
| Aqueous ammonia comprising 20% of $NH_3$ | 4.0 g |
| Demineralized water | q.s. for 100 g |

Method of Application

The above compositions were applied to natural grey hair comprising 90% of white hairs in a proportion of 30 g per 3 g of hair. After a setting time of 30 min on a heating plate at 27° C., the hair was rinsed, washed with a standard shampoo, and dried.

Results

The coloring of the hair was evaluated visually.

| Composition | Height of tone | Highlight |
|---|---|---|
| Composition A1 | Blond | Green |
| Composition A2 | Very light blond | Golden |
| Composition A8 | Dark blond | Chromatic deep purple |
| Composition A9 | Light blond | Iridescent natural |

-continued

| Composition | Height of tone | Highlight |
|---|---|---|
| Composition A10 | Blond | Blue |
| Composition A11 | Dark blond | Natural |
| Composition A13 | Light blond | Iridescent coppery |
| Composition A14 | Light blond | Iridescent natural |
| Composition A15 | Light blond | Ash natural |
| Composition A16 | Light blond | Coppery golden |

These shades were long-lasting and uniform.

Example 2

A composition comprising equimolar amounts of the following compound and the compound C2 described above was prepared. A long-lasting and uniform green-blue coloring was obtained by use of this composition in accordance with the present disclosure.

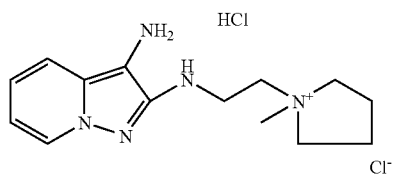

1-{2-[(3-Aminopyrazolo[1,5-a]pyridin-2-yl)amino]ethyl}-1-methylpyrrolidinium chloride

Example 3

A composition comprising equimolar amounts of the following compound and the compound C2 described above was prepared. A long-lasting and uniform green-blue coloring was obtained by use of this composition in accordance with the present disclosure.

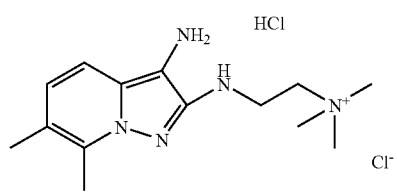

2-[(3-Amino-6,7-dimethylpyrazolo[1,5-a]pyridin-2-yl)amino]-N,N,N-trimethylethanaminium chloride

Example 4

A comparative composition A was prepared comprising:

| | | |
|---|---|---|
| Para-aminophenol | (0.0025 mol) | 0.28 g |
| 1-Methyl-2-hydroxy-4-aminobenzene | (0.0025 mol) | 0.31 g |
| Sodium sulfite | | 0.1 g |
| Oxyethylenated sodium lauryl ether sulfate (2.2 EO) as a 30% aqueous solution | | 1.0 g |
| Ethanol | | 5.0 g |
| Aqueous ammonia comprising 20% of $NH_3$ | | 4.0 g |
| Demineralized water | | q.s.p 100 g |

A composition B according to the present disclosure was prepared comprising:

| | | |
|---|---|---|
| 2-[(3-Aminopyrazolo[1,5-a]pyridin-2-yl)oxy]ethanol, HCl | (0.0025 mol) | 0.57 g |
| 1-Methyl-2-hydroxy-4-aminobenzene | (0.0025 mol) | 0.31 g |
| Sodium sulfite | | 0.1 g |
| Oxyethylenated sodium lauryl ether sulfate (2.2 EO) as a 30% aqueous solution | | 1.0 g |
| Ethanol | | 5.0 g |
| Aqueous ammonia comprising 20% of $NH_3$ | | 4.0 g |
| Demineralized water | | q.s.p. 100 g |

Method of Application

The resulting compositions were applied on grey hair comprising 90% of white hair (30 g for 3 g of hair). After a setting time of 30 min at 27° C., the hair was rinsed, shampooed, and dried.

Results

The coloring of the hair was evaluated visually. The results are reported in the following table.

| Composition | Height of tone | Highlight |
|---|---|---|
| Comparative Composition A | very light blond | Coppery golden |
| Composition B (present disclosure) | light blond | Iridescent coppery |

The composition B according to the present disclosure provided a more intense and chromatic color on the hair than the color obtained from comparative composition A.

What is claimed is:

1. A method for coloring keratinous fibers comprising applying to the fibers a composition comprising, in a medium appropriate for dyeing, at least one aminopyrazolopyridine oxidation base chosen from compounds of formula (I) and compounds of formula (II):

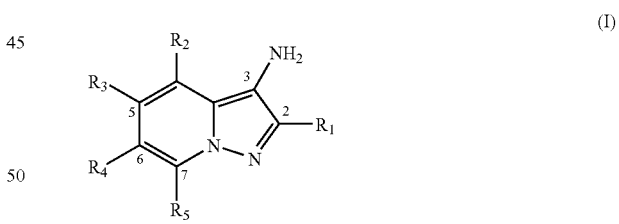

wherein:

$R_1$, $R_2$, $R_3$, $R_4$ and $R_5$, are, independently of one another, chosen from hydrogen atoms; halogen atoms; —$NHSO_3H$ radicals; hydroxyl radicals; ($C_1$-$C_4$)alkyl radicals; ($C_1$-$C_4$)alkoxy radicals; ($C_1$-$C_4$)alkylthio radicals; mono($C_1$-$C_4$)alkylamino radicals; di($C_1$-$C_4$)alkylamino radicals wherein the two alkyl groups can optionally, jointly with the nitrogen atom to which they are bonded, form a ring which can be interrupted by at least one heteroatom chosen from nitrogen, oxygen, and sulfur atoms; heterocycles; nitro radicals; phenyl radicals, carbonyl radicals; ($C_1$-$C_4$)alkoxycarbonyl radicals; carboxamido radicals; cyano radicals; amino radicals; sulfonyl radicals; —CO₂H radicals; —SO₃H radicals; —PO₃H₂ radicals; —PO₄H₂ radicals; groups of formula:

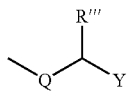

wherein R''' is chosen from oxygen atoms and nitrogen atoms, Q is chosen from oxygen atoms, NH groups, and NH(C₁-C₄)alkyl groups, and Y is chosen from hydroxyl, amino, (C₁-C₄)alkyl, (C₁-C₄)alkoxy, (C₁-C₄)alkylamino, and di(C₁-C₄)alkylamino radicals;

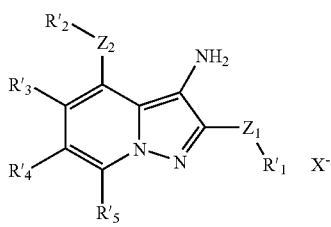

wherein:
R'₁ and R'₂ are, independently of each other, chosen from:
hydrogen atoms,
optionally substituted (C₁-C₁₀)alkyl radicals, optionally interrupted by at least one heteroatom chosen from O, N, Si, and S, and optionally interrupted by at least one group chosen from SO and SO₂,
halogen atoms,
SO₃H radicals,
substituted and unsubstituted, saturated, unsaturated, and aromatic 5- to 8-membered rings, optionally comprising at least one heteroatom chosen from N, O, and S, and optionally comprising at least one group chosen from SO₂ and —CO—, it being understood that the ring may optionally be cationic and/or substituted by a cationic radical,
—N⁺R₁₇R₁₈R₁₉ groups, wherein R₁₇, R₁₈, and R₁₉ are, independently of one another, chosen from linear and branched (C₁-C₅)alkyls, optionally substituted by at least one hydroxyl group,
Z₁ and Z₂ are, independently of one another, chosen from:
simple covalent bonds,
divalent radicals chosen from:
—O(CH₂)ₚ— radicals, wherein p is an integer ranging from 0 to 6,
—NR'₆(CH₂)_q(C₆H₄)_t— radicals, wherein q is an integer ranging from 0 to 6, t is chosen from 0 and 1, and R'₆ is chosen from hydrogen atoms and (C₁-C₆)alkyl radicals optionally substituted by at least one hydroxyl group,
when R'₁ is a methyl radical, Z₁ can also be chosen from divalent —S—, —SO—, and —SO₂— radicals,
when Z₁ is a covalent bond, R'₁ can also be chosen from:
optionally substituted (C₁-C₆)alkylcarbonyl radicals,
—O—CO—R, —CO—O—R, —NR—CO—R', and —CO—NRR' radicals, wherein R and R' are, independently of one another, chosen from hydrogen atoms and optionally substituted (C₁-C₆)alkyl radicals, when Z₂ is a covalent bond, R'₂ can also be chosen from:
optionally substituted (C₁-C₆)alkylcarbonyl radicals,
—O—CO—R, —CO—O—R, —NR—CO—R', and —CO—NRR' radicals, wherein R and R' are, independently of one another, chosen from hydrogen atoms and optionally substituted (C₁-C₆)alkyl radicals,
R'₃, R'₄, and R'₅, are, independently of one another, chosen from:
hydrogen atoms,
hydroxyl radicals,
(C₁-C₆)alkoxy radicals,
(C₁-C₆)alkylthio radicals,
amino radicals,
monoalkylamino radicals,
(C₁-C₆)dialkylamino radicals in which the alkyl radicals can form, with the nitrogen atom to which they are attached, a saturated or unsaturated, aromatic or non-aromatic, 5- to 8-membered heterocycle which can comprise at least one heteroatom chosen from N, O, and S, and at least one groups chosen from SO₂ and CO, it being understood that the heterocycle may optionally be cationic and/or substituted by a cationic radical,
optionally substituted (C₁-C₆)alkylcarbonyl radicals,
—O—CO—R, —CO—O—R, —NR—CO—R' and —CO—NRR' radicals, wherein R and R' are as defined above,
halogen atoms,
—NHSO₃H radicals,
optionally substituted (C₁-C₄)alkyl radicals,
saturated, unsaturated, and aromatic carbon rings, optionally substituted,
wherein it is understood that R'₃, R'₄, and R'₅ can form, in pairs, a saturated or unsaturated ring,
X⁻ is chosen from electronegative ions and groups of ions,
wherein it is understood that at least one of the groups R'₁ and R'₂ is chosen from cationic radicals;
with the proviso that the method is performed without the addition of any oxidizing agent, not including atmospheric oxygen.

2. The method according to claim 1, wherein the at least one compound of formula (I) is chosen from compounds of subformula (Ia), the acid addition salts thereof, and the base addition salts thereof:

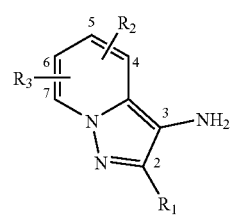

wherein:
R₁, R₂, and R₃, are, independently of one another, chosen from hydrogen atoms; halogen atoms; hydroxyl radicals; (C₁-C₄)alkyl radicals; (C₁-C₄)alkylthio radicals; (C₁-C₄)alkoxy radicals; —NHSO₃H radicals; amino radicals; (C₁-C₄)alkylamino radicals; di(C₁-C₄)alkylamino radicals wherein the two alkyl groups can, jointly with the nitrogen atom to which they are bonded, form a ring which can be interrupted by at least one heteroatom chosen from nitrogen, oxygen, and sulfur atoms; heterocycles; sulfonamido radicals; carbonyl radicals; (C₁-C₄) alkoxycarbonyl radicals; carboxamido radicals; and groups of formula:

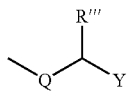

wherein R'" is chosen from oxygen atoms and nitrogen atoms, Q is chosen from oxygen atoms, NH groups, and NH(C₁-C₄)alkyl groups, and Y is chosen from hydroxyl, amino, C₁-C₄ alkyl, (C₁-C₄)alkoxy, (C₁-C₄)alkylamino, and di(C₁-C₄)alkylamino radicals.

3. The method according to claim 1, wherein the at least one aminopyrazolopyridine oxidation base is chosen from:
pyrazolo[1,5-a]pyridin-3-ylamine;
2-acetylaminopyrazolo[1,5-a]pyridin-3-ylamine;
2-(morpholin-4-yl)pyrazolo[1,5-a]pyridin-3-ylamine;
3-aminopyrazolo[1,5-a]pyridine-2-carboxylic acid;
2-methoxypyrazolo[1,5-a]pyridin-3-ylamine;
(3-aminopyrazolo[1,5-a]pyridin-7-yl)methanol;
2-(3-aminopyrazolo[1,5-a]pyridin-5-yl)ethanol;
2-(3-aminopyrazolo[1,5-a]pyridin-7-yl)ethanol;
(3-aminopyrazolo[1,5-a]pyridin-2-yl)methanol;
3,6-diaminopyrazolo[1,5-a]pyridine;
3,4-diaminopyrazolo[1,5-a]pyridine;
pyrazolo[1,5-a]pyridine-3,7-diamine;
7-(morpholin-4-yl)pyrazolo[1,5-a]pyridin-3-ylamine;
pyrazolo[1,5-a]pyridine-3,5-diamine;
5-(morpholin-4-yl)pyrazolo[1,5-a]pyridin-3-ylamine;
2-[(3-aminopyrazolo[1,5-a]pyridin-5-yl)(2-hydroxyethyl)amino]ethanol;
2-[(3-aminopyrazolo[1,5-a]pyridin-7-yl)(2-hydroxyethyl)amino]ethanol;
3-aminopyrazolo[1,5-a]pyridin-5-ol;
3-aminopyrazolo[1,5-a]pyridin-4-ol;
3-aminopyrazolo[1,5-a]pyridin-6-ol;
3-aminopyrazolo[1,5-a]pyridin-7-ol;
2-methoxy-6,7-dimethylpyrazolo[1,5-a]pyridin-3-amine;
2-[(3-aminopyrazolo[1,5-a]pyridin-2-yl)oxy]-ethanol;
4-ethyl-2-methoxy-7-methylpyrazolo[1,5-a]pyridin-3-amine hydrochloride;
1-(3-aminopyrazolo[1,5-a]pyridin-2-yl)pyrrolidin-3-ol;
2,2'-[(3-aminopyrazolo[1,5-a]pyridin-2-yl)imino]diethanol;
2-[(3-aminopyrazolo[1,5-a]pyridin-2-yl)amino]-ethanol;
N2-(2-(pyridin-3-yl)ethyl)pyrazolo[1,5-a]pyridine-2,3-diamine;
the acid addition salts thereof; and the base addition salts thereof.

4. The method according to claim 1, wherein at least one of $Z_1$ and/or $Z_2$ is chosen from covalent bonds, —NR'₆(CH₂)_q— radicals, and —O(CH₂)_p— radicals, and at least one of R'₁ and/or R'₂ is a cationic radical.

5. The method according to claim 4, wherein at least one of R'₁ and/or R'₂ is chosen from imidazoles substituted by a quaternary ammonium radical, imidazoliums, piperazines substituted by a quaternary ammonium radical, piperaziniums, pyrrolidines substituted by a quaternary ammonium radical, pyrrolidiniums, diazepanes substituted by a quaternary ammonium radical, and diazepaniums.

6. The method according to claim 4, wherein R'₁ and R'₁ are, independently of one another, chosen from hydrogen atoms, trialkylammonium, tri(hydroxyalkyl)ammonium, (hydroxyalkyl)dialkylammonium, and di(hydroxyalkyl)alkylammonium groups.

7. The method according to claim 1, wherein R'₃, R'₄, and R'₅ are, independently of one another, chosen from hydrogen atoms and optionally substituted (C₁-C₄)alkyl radicals.

8. The method according to claim 1, wherein the at least one compound of formula (II) is chosen from compounds of subformula (IIa):

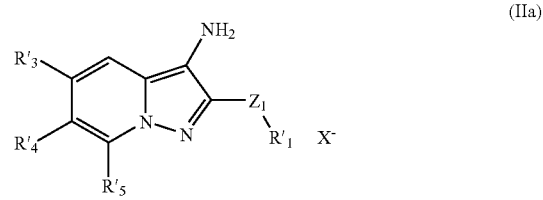

wherein $Z_1$, R'₁, R'₃, R'₄, and R'₅ are as defined in claim 1.

9. The method according to claim 8, wherein $Z_1$ is chosen from covalent bonds, —NR'₆(CH₂)_q— radicals, and —O(CH₂)_p— radicals, and wherein R'₁ is a cationic radical.

10. The method according to claim 1, wherein the at least one compound of formula (II) is chosen from:

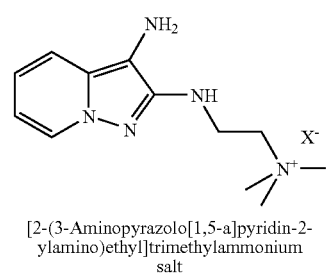

[2-(3-Aminopyrazolo[1,5-a]pyridin-2-ylamino)ethyl]trimethylammonium salt

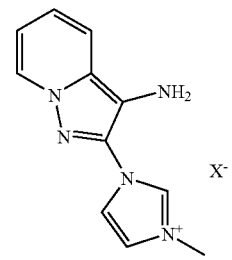

3-(3-Aminopyrazolo[1,5-a]pyridin-2-yl)-1-methyl-3H-imidaol-1-ium salt

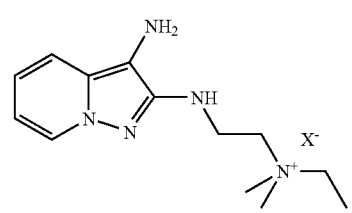

[2-(3-Aminopyrazolo[1,5-a]pyridin-2-ylamino)ethyl]ethyldimethylammonium salt

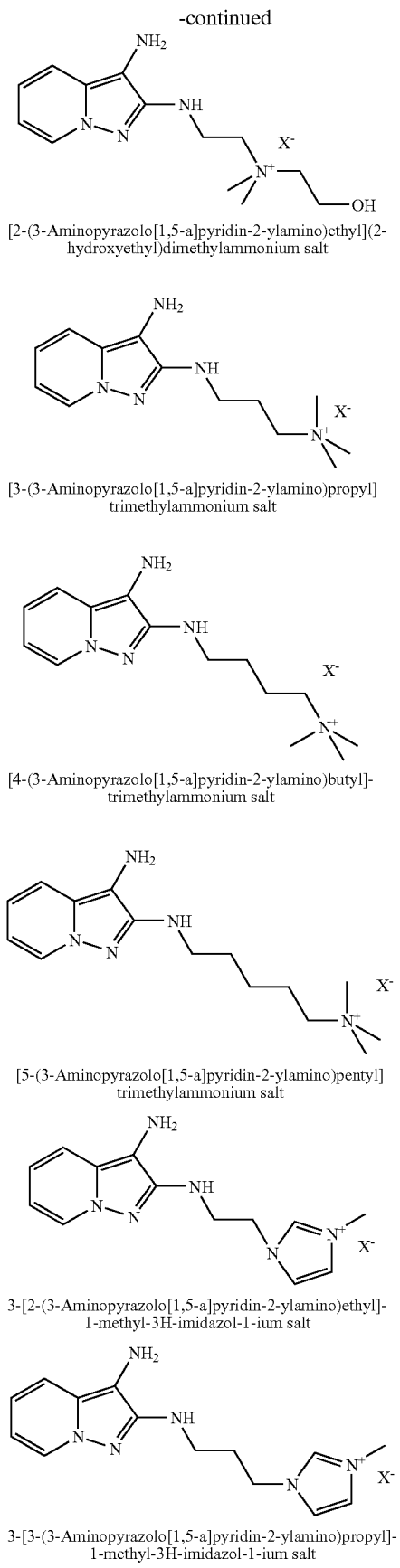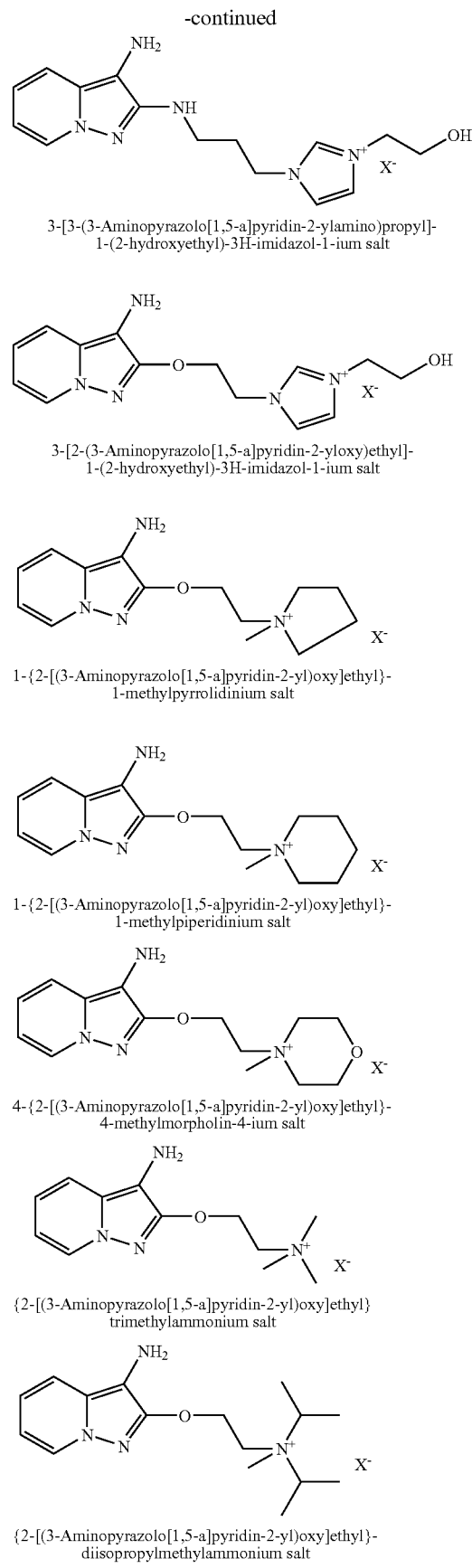

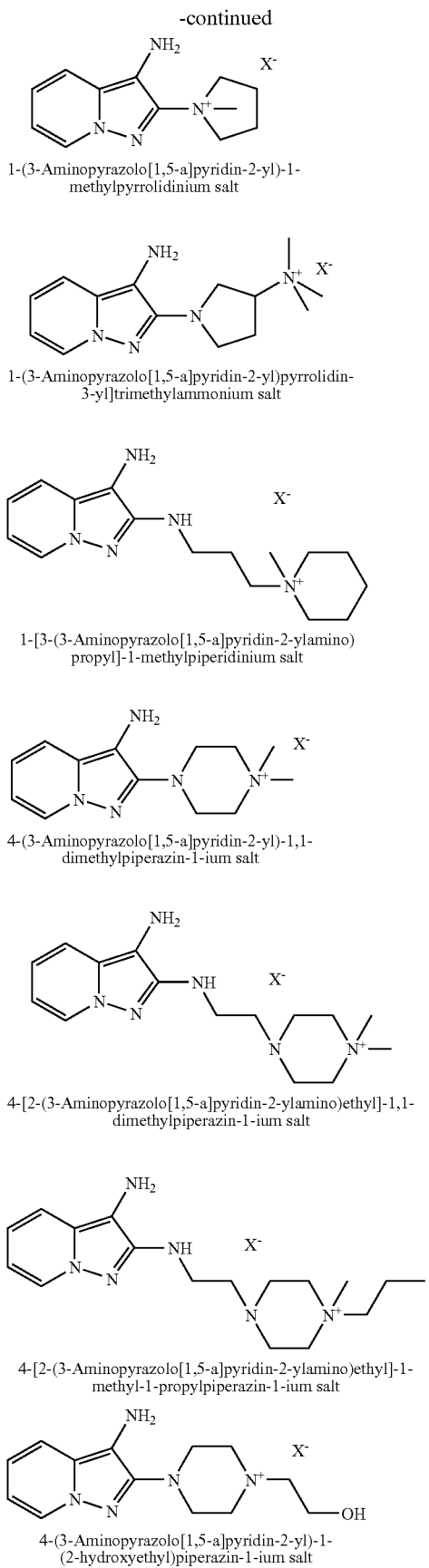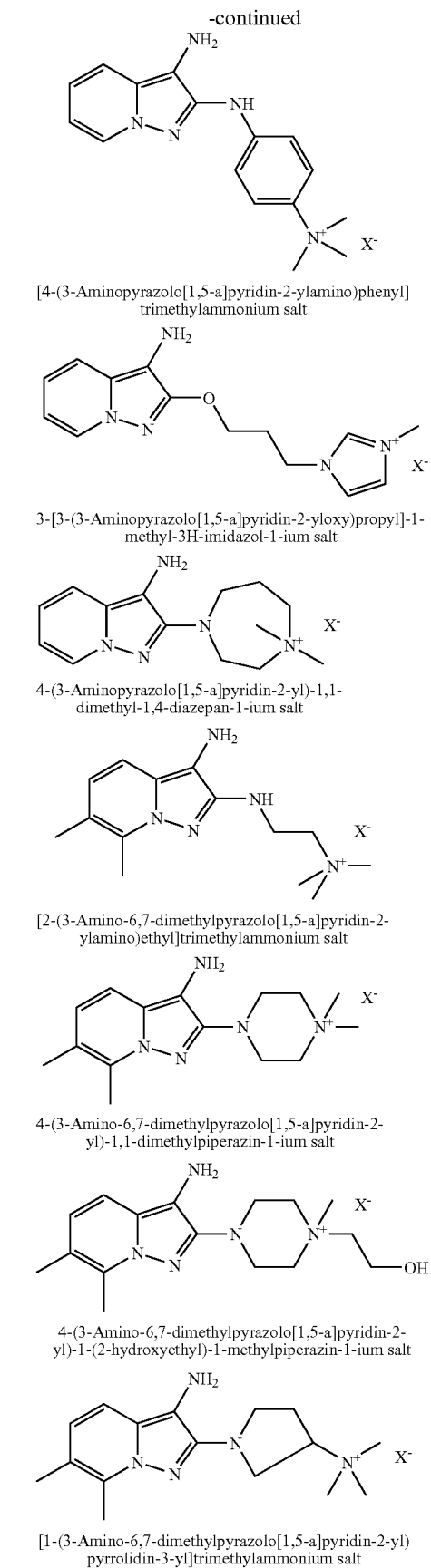

-continued

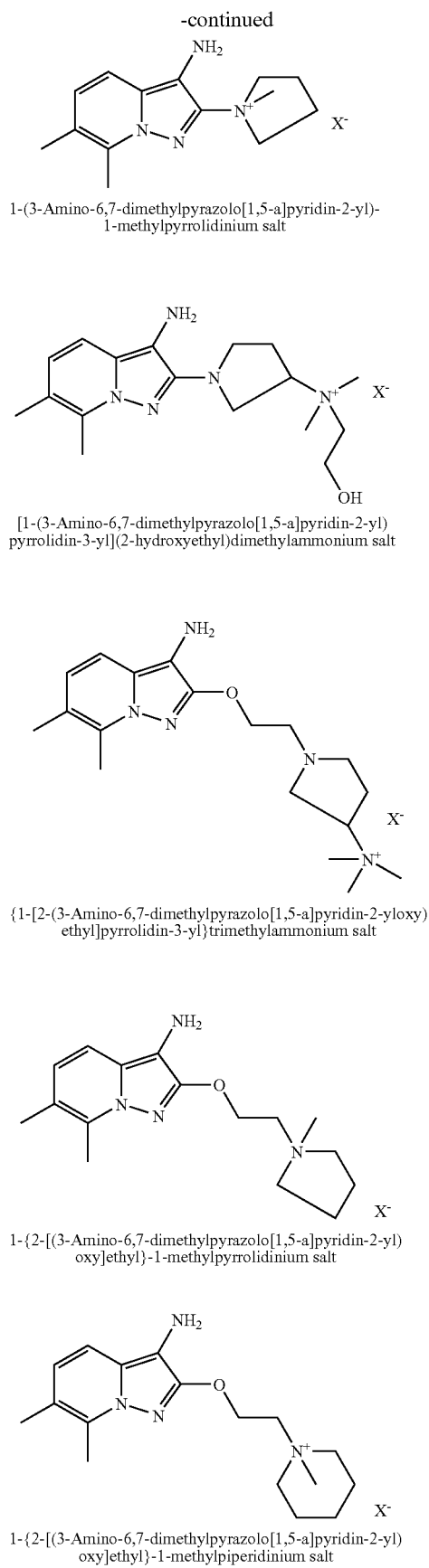

1-(3-Amino-6,7-dimethylpyrazolo[1,5-a]pyridin-2-yl)-
1-methylpyrrolidinium salt

[1-(3-Amino-6,7-dimethylpyrazolo[1,5-a]pyridin-2-yl)
pyrrolidin-3-yl](2-hydroxyethyl)dimethylammonium salt {1-[2-(3-Amino-6,7-dimethylpyrazolo[1,5-a]pyridin-2-yloxy)
ethyl]pyrrolidin-3-yl}trimethylammonium salt 1-{2-[(3-Amino-6,7-dimethylpyrazolo[1,5-a]pyridin-2-yl)
oxy]ethyl}-1-methylpyrrolidinium salt 1-{2-[(3-Amino-6,7-dimethylpyrazolo[1,5-a]pyridin-2-yl)
oxy]ethyl}-1-methylpiperidinium salt -continued

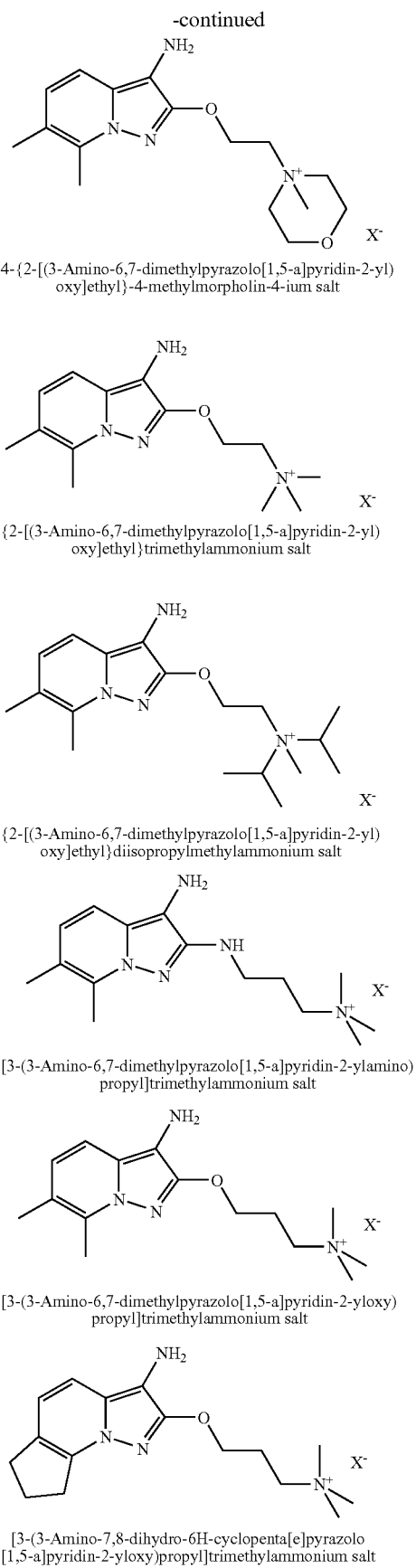

4-{2-[(3-Amino-6,7-dimethylpyrazolo[1,5-a]pyridin-2-yl)
oxy]ethyl}-4-methylmorpholin-4-ium salt {2-[(3-Amino-6,7-dimethylpyrazolo[1,5-a]pyridin-2-yl)
oxy]ethyl}trimethylammonium salt {2-[(3-Amino-6,7-dimethylpyrazolo[1,5-a]pyridin-2-yl)
oxy]ethyl}diisopropylmethylammonium salt

[3-(3-Amino-6,7-dimethylpyrazolo[1,5-a]pyridin-2-ylamino)
propyl]trimethylammonium salt

[3-(3-Amino-6,7-dimethylpyrazolo[1,5-a]pyridin-2-yloxy)
propyl]trimethylammonium salt

[3-(3-Amino-7,8-dihydro-6H-cyclopenta[e]pyrazolo
[1,5-a]pyridin-2-yloxy)propyl]trimethylammonium salt -continued

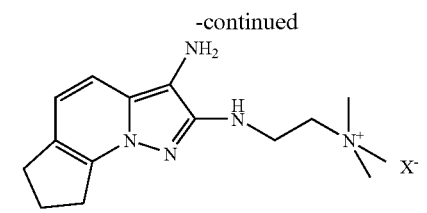

{2-[(3-Amino-7,8-dihydro-6H-cyclopenta[e]pyrazolo[1,5-a]pyridin-2-yl)amino]ethyl}trimethylammonium salt

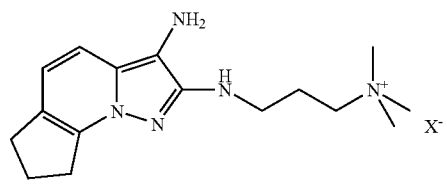

{3-[(3-Amino-7,8-dihydro-6H-cyclopenta[e]pyrazolo[1,5-a]pyridin-2-yl)amino]propyl}trimethylammonium salt

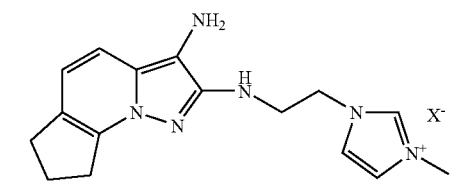

1-{2-[(3-Amino-7,8-dihydro-6H-cyclopenta[e]pyrazolo[1,5-a]pyridin-2-yl)amino]ethyl}-3-methyl-1H-imidazol-3-ium salt

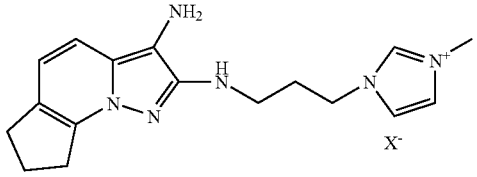

1-{3-[(3-Amino-7,8-dihydro-6H-cyclopenta[e]pyrazolo[1,5-a]pyridin-2-yl)amino]propyl}-3-methyl-1H-imidazol-3-ium salt

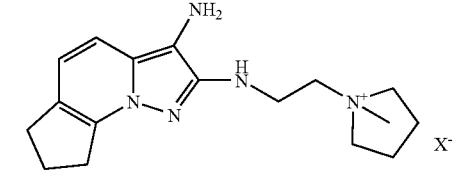

1-{2-[(3-Amino-7,8-dihydro-6H-cyclopenta[e]pyrazolo[1,5-a]pyridin-2-yl)amino]ethyl}-1-methylpyrrolidinium salt

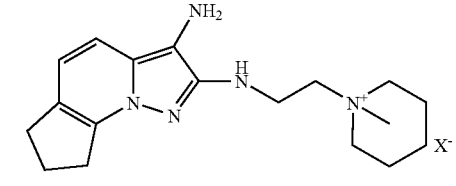

1-{2-[(3-Amino-7,8-dihydro-6H-cyclopenta[e]pyrazolo[1,5-a]pyridin-2-yl)amino]ethyl}-1-methylpiperidinium salt

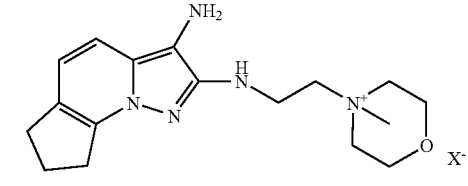

4-{2-[(3-Amino-7,8-dihydro-6H-cyclopenta[e]pyrazolo[1,5-a]pyridin-2-yl)amino]ethyl}-4-methylmorpholin-4-ium salt -continued

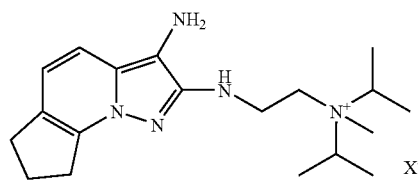

{2-[(3-Amino-7,8-dihydro-6H-cyclopenta[e]pyrazolo[1,5-a]pyridin-2-yl)amino]ethyl}diisopropylmethylammonium salt

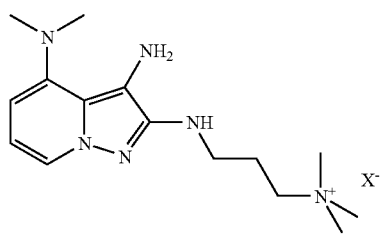

[3-(3-Amino-4-(dimethylamino)pyrazolo[1,5-a]pyridin-2-ylamino)propyl]trimethylammonium salt

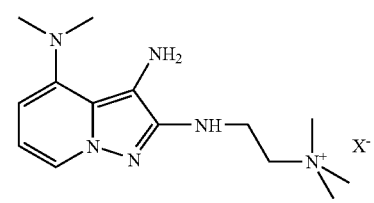

[2-(3-Amino-4-(dimethylamino)pyrazolo[1,5-a]pyridin-2-ylamino)ethyl]trimethylammonium salt

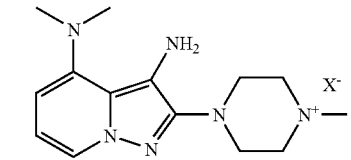

4-(3-Amino-4-(dimethylamino)pyrazolo[1,5-a]pyridin-2-yl)-1-methylpiperazin-1-ium salt

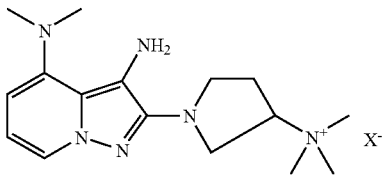

[1-(3-Amino-4-(dimethylamino)pyrazolo[1,5-a]pyridin-2-yl)pyrrolidin-3-yl]trimethylammonium salt

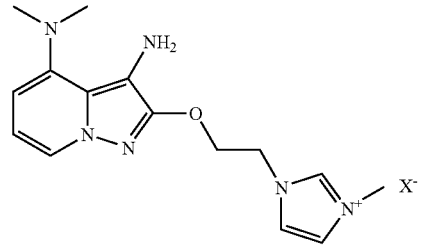

3-[2-(3-Amino-4-(dimethylamino)pyrazolo[1,5-a]pyridin-2-yloxy)ethyl]-1-methyl-3H-imidazol-1-ium salt -continued

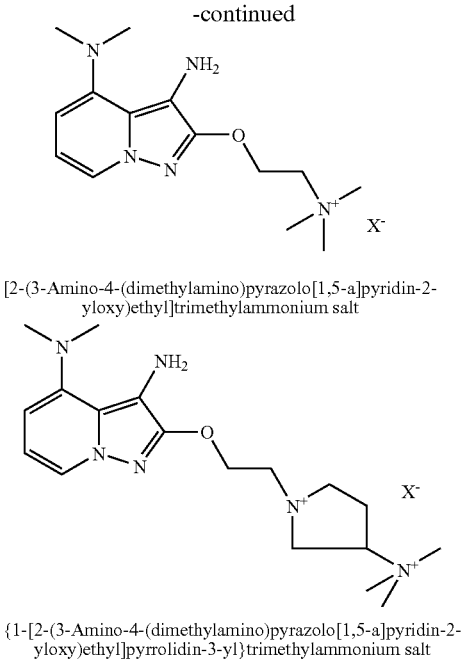

[2-(3-Amino-4-(dimethylamino)pyrazolo[1,5-a]pyridin-2-yloxy)ethyl]trimethylammonium salt {1-[2-(3-Amino-4-(dimethylamino)pyrazolo[1,5-a]pyridin-2-yloxy)ethyl]pyrrolidin-3-yl}trimethylammonium salt -continued

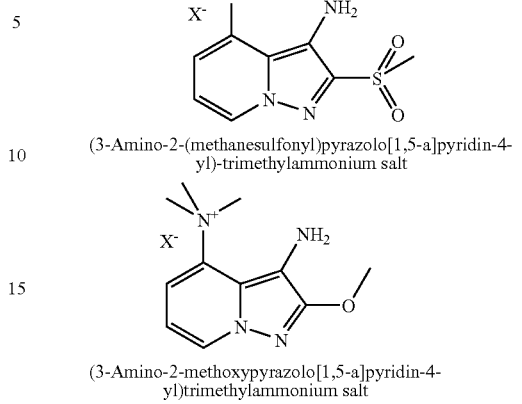

(3-Amino-2-(methanesulfonyl)pyrazolo[1,5-a]pyridin-4-yl)-trimethylammonium salt (3-Amino-2-methoxypyrazolo[1,5-a]pyridin-4-yl)trimethylammonium salt 11. The method according to claim 1, wherein the dyeing composition further comprises at least one coupler chosen from meta-phenylenediamines, meta-aminophenols, meta-diphenols, naphthalene couplers, heterocyclic couplers, and their addition salts.

* * * * *

UNITED STATES PATENT AND TRADEMARK OFFICE
CERTIFICATE OF CORRECTION

PATENT NO. : 7,648,536 B2
APPLICATION NO. : 12/149871
DATED : January 19, 2010
INVENTOR(S) : Jean-Baptiste Saunier It is certified that error appears in the above-identified patent and that said Letters Patent is hereby corrected as shown below:

In claim 1, column 24, line 65, "radicals," should read --radicals;--.

In claim 1, column 26, line 21, "groups" should read --group--.

In claim 6, column 27, line 66, "$R'_1$ and $R'_1$" should read --$R'_1$ and $R'_2$--.

In claim 10, column 38, line 19, "salt" should read --salt.--.

Signed and Sealed this

Thirtieth Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,648,536 B2  Page 1 of 1
APPLICATION NO. : 12/149871
DATED : January 19, 2010
INVENTOR(S) : Jean-Baptiste Saunier It is certified that error appears in the above-identified patent and that said Letters Patent is hereby corrected as shown below:

In column 2, lines 30-35, " 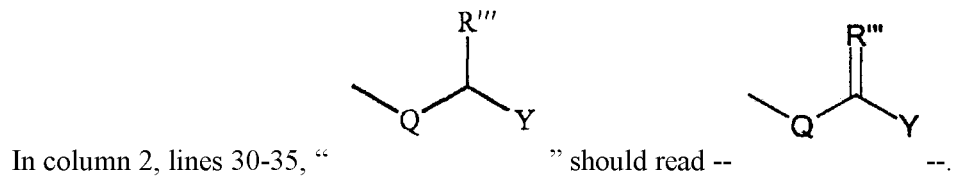 " should read -- --.

In column 5, lines 30-35, " 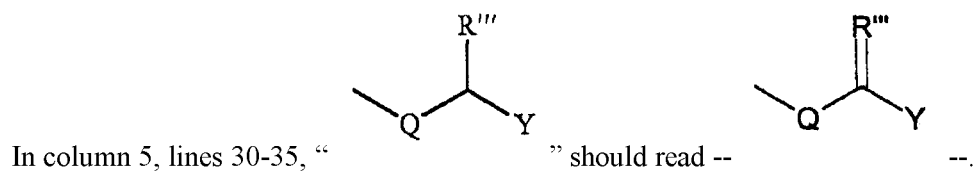 " should read -- --.

In column 6, lines 5-10, " 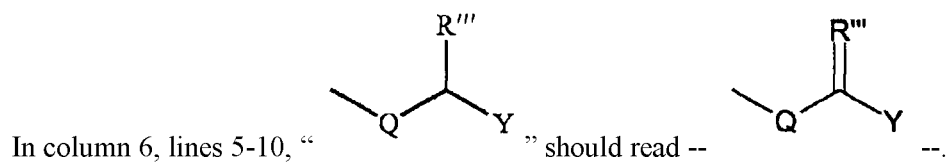 " should read -- --.

In claim 1, column 25, lines 5-10, " 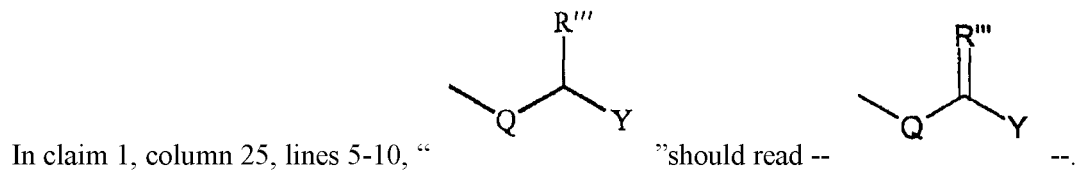 " should read -- --.

In claim 2, column 27, lines 5-10, " 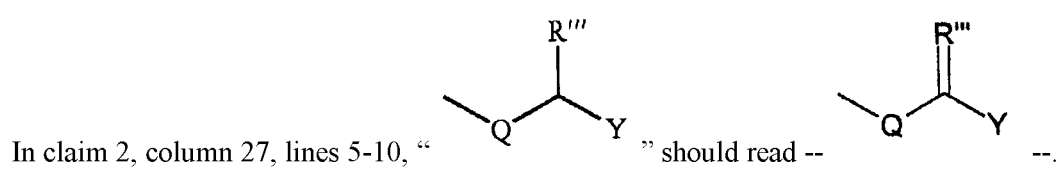 " should read -- --.

Signed and Sealed this

First Day of June, 2010

David J. Kappos
*Director of the United States Patent and Trademark Office*